US006479629B2

(12) United States Patent
Baldwin et al.

(10) Patent No.: US 6,479,629 B2
(45) Date of Patent: Nov. 12, 2002

(54) MAIZE HISTONE DEACETYLASES AND THEIR USE

(75) Inventors: Donald Adelphi Baldwin, Des Moines, IA (US); Steven P. Briggs, Del Mar, CA (US); Virginia C. Crane, Des Moines, CA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/883,720

(22) Filed: Jun. 18, 2001

(65) Prior Publication Data

US 2002/0022256 A1 Feb. 21, 2002

Related U.S. Application Data

(62) Division of application No. 09/282,305, filed on Mar. 31, 1999, now Pat. No. 6,287,843.
(60) Provisional application No. 60/080,563, filed on Apr. 3, 1998.

(51) Int. Cl.[7] .............................................. A61K 38/00
(52) U.S. Cl. .................... 530/324; 424/94.1; 536/23.2; 800/279
(58) Field of Search ....................... 530/324; 424/94.1; 536/23.2; 800/279

(56) References Cited

PUBLICATIONS

Brosch, et al., "Purification and Characterization of a High Molecular Weight Histone Deacetylase Complex (HD2) of Maize Embryos," *Biochemistry*, 1996, pp. 15907–15914, vol. 35, American Chemical Society.

De Rubertis, et al., "The Histone Deacetylase RPD3 Counteracts Genomic Silencing in Drosophila and Yeast," *Nature*, 1996, pp. 589–591, vol. 384.

Lusser, et al., "Identification of Maize Histone Deacetylase HD2 as an Acidic Nuclear Phosphoprotein," *Science*, Jul. 1997, pp. 88–91, vol. 277.

Ransom, R., and Walton, J., "Histone Hyperacetylation in Maize in Response to Treatment with HC–Toxin or Infection by the Filamentous Fungus Cochliobolus Carbonum," *Plant Pysiol.*, 1997, pp. 1021–1027, vol. 115.

Rossi, et al., "Identification and Characterization of an RPD3 homologue from Maize (Zea mays L.) that is able to Complement an rpd3 Null Mutant of Saccharomyces Cerevisiae", *Mol. Gen. Genet*, 1998, pp. 288–296, vol. 258.

Rundlett, et al., "HDA1 and RPD3 are Members of Distinct Yeast Histone Deacetylase Complexes that Regulate Silencing and Transcription," *Proc. Natl. Acad. Sci.* USA, Dec. 1996, pp. 14503–14508, vol. 93.

Taunton, et al., "A Mammalian Histone Deacetylase Related to the Yeast Transcriptional Regulator Rpd3p," *Science*, Apr. 19, 1996, pp. 408–411, vol. 272.

EMBL Database for Accession No. AFO35815, Dec. 9, 1997 (XP002120446).
EMBL Database for Accession No. AFO14824 (XP002120447).
EMBL Database for Accession No. AFO45473 (XP002120448).

*Primary Examiner*—Hankyel T. Park
(74) *Attorney, Agent, or Firm*—Alston & Bird LLP

(57) ABSTRACT

Histone deacetylases and nucleotide sequences encoding said histone deacetylases are provided. The sequences as well as corresponding antisense constructs are useful for modulating gene activity in plants. Additionally, the sequences are useful for enhancing disease resistance in transformed plants.

9 Claims, 1 Drawing Sheet

SEQUENCE LISTING

```
<160> NUMBER OF SEQ ID NOS: 18

<210> SEQ ID NO 1
<211> LENGTH: 1826
<212> TYPE: DNA
<213> ORGANISM: Zea mays
<220> FEATURE:
<221> NAME/KEY: CDS
<222> LOCATION: (29)..(1405)
```

<400> SEQUENCE: 1

```
ggcacgagct tcaaccatct caggcgga atg gcg gct tct ggt gag ggc gcg        52
                                Met Ala Ala Ser Gly Glu Gly Ala
                                 1               5 tcg ctg ccg tct ccg gcg ggc ggg gag gat gcg cac cgc cgc gtc          100
Ser Leu Pro Ser Pro Ala Gly Gly Glu Asp Ala His Arg Arg Val
     10              15              20 agc tat ttc tac gag ccg tcg atc gga gac tac tac tac ggg caa ggt     148
Ser Tyr Phe Tyr Glu Pro Ser Ile Gly Asp Tyr Tyr Tyr Gly Gln Gly
 25              30              35              40 cac ccg atg aag ccc cac cgc atc cga atg gcg cac tcg ctg gtg gtc     196
His Pro Met Lys Pro His Arg Ile Arg Met Ala His Ser Leu Val Val
             45              50              55 cac tac ggc ctc cac cgc ctc ctc gag ctc tcc cgc ccc tac ccg gcc     244
His Tyr Gly Leu His Arg Leu Leu Glu Leu Ser Arg Pro Tyr Pro Ala
         60              65              70 tct gag gcc gac atc cgc cgc ttc cac tcc gac gac tac gtc gct ttc     292
Ser Glu Ala Asp Ile Arg Arg Phe His Ser Asp Asp Tyr Val Ala Phe
     75              80              85 ctc gcg tcc gcc acc gga aac ccg ggt gtc ctc gac ccg cgc gcc att     340
Leu Ala Ser Ala Thr Gly Asn Pro Gly Val Leu Asp Pro Arg Ala Ile
         90              95             100 aag cgc ttt aac gtc ggt gag gac tgc ccc gtg ttc gac ggt ctc ttc     388
Lys Arg Phe Asn Val Gly Glu Asp Cys Pro Val Phe Asp Gly Leu Phe
105             110             115             120 ccc ttc tgc cag gcc tcc gct ggg gga agc atc ggc gcc gcc gtc aag     436
Pro Phe Cys Gln Ala Ser Ala Gly Gly Ser Ile Gly Ala Ala Val Lys
             125             130             135 ctt aac cgc ggg gac gcc gac atc acc gtc aac tgg gcg ggc ggc ctc     484
Leu Asn Arg Gly Asp Ala Asp Ile Thr Val Asn Trp Ala Gly Gly Leu
         140             145             150 cac cac gcc aag aag agc gag gcc tcc ggg ttc tgc tac gtc aac gac     532
His His Ala Lys Lys Ser Glu Ala Ser Gly Phe Cys Tyr Val Asn Asp
     155             160             165 atc gtc ctc gcc atc ctc gag ctc ctc aag ttc cac agg cgt gtg cta     580
Ile Val Leu Ala Ile Leu Glu Leu Leu Lys Phe His Arg Arg Val Leu
170             175             180 tat gta gac att gat gtc cac cat gga gat ggc gtg gag gag gcc ttc     628
Tyr Val Asp Ile Asp Val His His Gly Asp Gly Val Glu Glu Ala Phe
185             190             195             200 ttc act aca aac cga gtc atg act gtt tcc ttt cac aag tat ggg gat     676
Phe Thr Thr Asn Arg Val Met Thr Val Ser Phe His Lys Tyr Gly Asp
             205             210             215 ttt ttc cct ggt act gga cat atc act gac gtt ggg gca gcc gaa ggg     724
Phe Phe Pro Gly Thr Gly His Ile Thr Asp Val Gly Ala Ala Glu Gly
         220             225             230 aag cat tat gct ctg aat gtt ccc ctg agt gat ggt atc gat gac acc     772
Lys His Tyr Ala Leu Asn Val Pro Leu Ser Asp Gly Ile Asp Asp Thr
     235             240             245 acc ttt cgt ggt ctg ttt caa tgc atc att aag aaa gtt atg gag gtt     820
Thr Phe Arg Gly Leu Phe Gln Cys Ile Ile Lys Lys Val Met Glu Val
250             255             260 tat cag cca gac gtg gtt gtc ctc caa tgc gga gct gac tct ttg gct     868
Tyr Gln Pro Asp Val Val Val Leu Gln Cys Gly Ala Asp Ser Leu Ala
265             270             275             280 gga gac agg tta ggt tgc ttc aac ctg tct gtg aag ggt cat gct gac     916
Gly Asp Arg Leu Gly Cys Phe Asn Leu Ser Val Lys Gly His Ala Asp
             285             290             295
```

| | | |
|---|---|---|
| tgc ctc cgt ttc ctt agg tcg tac aat gtt cct atg atg gtt tta ggt<br>Cys Leu Arg Phe Leu Arg Ser Tyr Asn Val Pro Met Met Val Leu Gly<br>           300                         305                    310 | 964 |
| ggt gga ggt tac acc atc aga aat gtt gca cgc tgc tgg tgc tac gag<br>Gly Gly Gly Tyr Thr Ile Arg Asn Val Ala Arg Cys Trp Cys Tyr Glu<br>               315                      320                    325 | 1012 |
| acc gca gtt gct gtt gga gtt gaa cct gat aac aag ctg cct tac aat<br>Thr Ala Val Ala Val Gly Val Glu Pro Asp Asn Lys Leu Pro Tyr Asn<br> 330                         335                    340 | 1060 |
| gat tac tat gag tac ttt ggc cct gat tat act ctt cat atc caa cca<br>Asp Tyr Tyr Glu Tyr Phe Gly Pro Asp Tyr Thr Leu His Ile Gln Pro<br>345                         350                    355                360 | 1108 |
| aaa agt gtt gaa aac ctg aat acc aca aag gac ttg gag aac ata aag<br>Lys Ser Val Glu Asn Leu Asn Thr Thr Lys Asp Leu Glu Asn Ile Lys<br>               365                      370                    375 | 1156 |
| aac atg ata ttg gag aac ctg tca aag ata gaa cat gtt ccc agc act<br>Asn Met Ile Leu Glu Asn Leu Ser Lys Ile Glu His Val Pro Ser Thr<br> 380                         385                    390 | 1204 |
| caa ttc cat gac aga ccg tca gac cct gaa gct cca gag gag aaa gag<br>Gln Phe His Asp Arg Pro Ser Asp Pro Glu Ala Pro Glu Glu Lys Glu<br>               395                      400                    405 | 1252 |
| gag gac atg gac aag agg cca cct cag cgc agc aga tta tgg agc gga<br>Glu Asp Met Asp Lys Arg Pro Pro Gln Arg Ser Arg Leu Trp Ser Gly<br>410                         415                    420 | 1300 |
| gga gct tac gac tct gat aca gag gat cct gac agc ctg aaa agc gag<br>Gly Ala Tyr Asp Ser Asp Thr Glu Asp Pro Asp Ser Leu Lys Ser Glu<br>425                       430                    435                440 | 1348 |
| ggt aaa gac gta act gct aac ttc cag atg aag gat gaa cca aaa gat<br>Gly Lys Asp Val Thr Ala Asn Phe Gln Met Lys Asp Glu Pro Lys Asp<br>                       445                    450                    455 | 1396 |
| gat ctg tag aagtttcaga agtgcccca aagttactga gttgtgaatg<br>Asp Leu | 1445 |
| ggatcgtcga catgcatgtt gaagagtggg gacgcatctg aacctgtccg tgctgatatc | 1505 |
| tgccgctgtg catctgtaac agactgaacg ttttgctggt tccagctttc ctgcgtgttg | 1565 |
| gtaactagac tagatatatg gcccttggt gggtcccaaa ctgttgagct ggagaaatga | 1625 |
| agtgattatt ctcgcatgat ttactgtagc atgcatgtaa tcattaccca ttagttcatt | 1685 |
| aggctatcaa cagtagttta ttcatcccca tattcaaact tcactatgcg cgcatacagt | 1745 |
| gatttgagtg accatatgga taaactttga agatgatttt tgggtagtgt ttggtttcga | 1805 |
| agtgtaaaaa aaaaaaaaaa a | 1826 |

<210> SEQ ID NO 2
<211> LENGTH: 458
<212> TYPE: PRT
<213> ORGANISM: Zea mays

<400> SEQUENCE: 2

Met Ala Ala Ser Gly Glu Gly Ala Ser Leu Pro Ser Pro Ala Gly Gly
1               5                  10                 15

Glu Asp Ala His Arg Arg Val Ser Tyr Phe Tyr Glu Pro Ser Ile
              20                  25                  30

Gly Asp Tyr Tyr Tyr Gly Gln Gly His Pro Met Lys Pro His Arg Ile
          35                      40                  45

Arg Met Ala His Ser Leu Val Val His Tyr Gly Leu His Arg Leu Leu
     50                     55                  60

Glu Leu Ser Arg Pro Tyr Pro Ala Ser Glu Ala Asp Ile Arg Arg Phe
65               70                  75                  80

```
His Ser Asp Asp Tyr Val Ala Phe Leu Ala Ser Ala Thr Gly Asn Pro
                85                  90                  95

Gly Val Leu Asp Pro Arg Ala Ile Lys Arg Phe Asn Val Gly Glu Asp
            100                 105                 110

Cys Pro Val Phe Asp Gly Leu Phe Pro Phe Cys Gln Ala Ser Ala Gly
            115                 120                 125

Gly Ser Ile Gly Ala Ala Val Lys Leu Asn Arg Gly Asp Ala Asp Ile
            130                 135                 140

Thr Val Asn Trp Ala Gly Gly Leu His His Ala Lys Lys Ser Glu Ala
145                 150                 155                 160

Ser Gly Phe Cys Tyr Val Asn Asp Ile Val Leu Ala Ile Leu Glu Leu
                165                 170                 175

Leu Lys Phe His Arg Arg Val Leu Tyr Val Asp Ile Asp Val His His
                180                 185                 190

Gly Asp Gly Val Glu Glu Ala Phe Phe Thr Thr Asn Arg Val Met Thr
            195                 200                 205

Val Ser Phe His Lys Tyr Gly Asp Phe Phe Pro Gly Thr Gly His Ile
            210                 215                 220

Thr Asp Val Gly Ala Ala Glu Gly Lys His Tyr Ala Leu Asn Val Pro
225                 230                 235                 240

Leu Ser Asp Gly Ile Asp Asp Thr Thr Phe Arg Gly Leu Phe Gln Cys
                245                 250                 255

Ile Ile Lys Lys Val Met Glu Val Tyr Gln Pro Asp Val Val Val Leu
                260                 265                 270

Gln Cys Gly Ala Asp Ser Leu Ala Gly Asp Arg Leu Gly Cys Phe Asn
            275                 280                 285

Leu Ser Val Lys Gly His Ala Asp Cys Leu Arg Phe Leu Arg Ser Tyr
            290                 295                 300

Asn Val Pro Met Met Val Leu Gly Gly Gly Tyr Thr Ile Arg Asn
305                 310                 315                 320

Val Ala Arg Cys Trp Cys Tyr Glu Thr Ala Val Ala Val Gly Val Glu
                325                 330                 335

Pro Asp Asn Lys Leu Pro Tyr Asn Asp Tyr Tyr Glu Tyr Phe Gly Pro
            340                 345                 350

Asp Tyr Thr Leu His Ile Gln Pro Lys Ser Val Glu Asn Leu Asn Thr
            355                 360                 365

Thr Lys Asp Leu Glu Asn Ile Lys Asn Met Ile Leu Glu Asn Leu Ser
            370                 375                 380

Lys Ile Glu His Val Pro Ser Thr Gln Phe His Asp Arg Pro Ser Asp
385                 390                 395                 400

Pro Glu Ala Pro Glu Glu Lys Glu Glu Asp Met Asp Lys Arg Pro Pro
                405                 410                 415

Gln Arg Ser Arg Leu Trp Ser Gly Gly Ala Tyr Asp Ser Asp Thr Glu
            420                 425                 430

Asp Pro Asp Ser Leu Lys Ser Glu Gly Lys Asp Val Thr Ala Asn Phe
            435                 440                 445

Gln Met Lys Asp Glu Pro Lys Asp Asp Leu
    450                 455

<210> SEQ ID NO 3
<211> LENGTH: 1475
<212> TYPE: DNA
<213> ORGANISM: Zea mays
<220> FEATURE:
```

```
<221> NAME/KEY: CDS
<222> LOCATION: (29)..(1084)

<400> SEQUENCE: 3
ccacgcgtcc gcaaccatct caggcgga atg gcg gct tct ggt gag ggc gcg         52
                              Met Ala Ala Ser Gly Glu Gly Ala
                                1               5 tcg ctg ccg tct ccg gcg ggc ggg gag gat gcg cac cgc cgc gtc          100
Ser Leu Pro Ser Pro Ala Gly Gly Glu Asp Ala His Arg Arg Val
    10                  15                  20 agc tat ttc tac gag ccg tcg atc gga gac tac tac ggg caa ggt          148
Ser Tyr Phe Tyr Glu Pro Ser Ile Gly Asp Tyr Tyr Gly Gln Gly
25                  30                  35                  40 cac ccg atg aag ccc cac cac gcc aag aag agc gag gcc tcc ggg ttc      196
His Pro Met Lys Pro His His Ala Lys Lys Ser Glu Ala Ser Gly Phe
                45                  50                  55 tgc tac gtc aac gac atc gtc ctc gcc atc ctc gag ctc ctc aag ttc      244
Cys Tyr Val Asn Asp Ile Val Leu Ala Ile Leu Glu Leu Leu Lys Phe
                60                  65                  70 cac agg cgt gtg cta tat gta gac att gat gtc cac cat gga gat ggc      292
His Arg Arg Val Leu Tyr Val Asp Ile Asp Val His His Gly Asp Gly
            75                  80                  85 gtg gag gag gcc ttc ttc act aca aac cga gtc atg act gtt tcc ttt      340
Val Glu Glu Ala Phe Phe Thr Thr Asn Arg Val Met Thr Val Ser Phe
        90                  95                  100 cac aag tat ggg gat ttt ttc cct ggt act gga cat atc act gac gtt      388
His Lys Tyr Gly Asp Phe Phe Pro Gly Thr Gly His Ile Thr Asp Val
105                 110                 115                 120 ggg gca gcc gaa ggg aag cat tat gct ctg aat gtt ccc ctg agt gat      436
Gly Ala Ala Glu Gly Lys His Tyr Ala Leu Asn Val Pro Leu Ser Asp
                125                 130                 135 ggt atc gat gac acc acc ttt cgt ggt ctg ttt caa tgc atc att aag      484
Gly Ile Asp Asp Thr Thr Phe Arg Gly Leu Phe Gln Cys Ile Ile Lys
                140                 145                 150 aaa gtt atg gag gtt tat cag cca gac gtg gtt gtc ctc caa tgc gga      532
Lys Val Met Glu Val Tyr Gln Pro Asp Val Val Val Leu Gln Cys Gly
            155                 160                 165 gct gac tct ttg gct gga gac agg tta ggt tgc ttc aac ctg tct gtg      580
Ala Asp Ser Leu Ala Gly Asp Arg Leu Gly Cys Phe Asn Leu Ser Val
        170                 175                 180 aag ggt cat gct gac tgc ctc cgt ttc ctt agg tcg tac aat gtt cct      628
Lys Gly His Ala Asp Cys Leu Arg Phe Leu Arg Ser Tyr Asn Val Pro
185                 190                 195                 200 atg atg gtt tta ggt ggt gga ggt tac acc atc aga aat gtt gca cgc      676
Met Met Val Leu Gly Gly Gly Gly Tyr Thr Ile Arg Asn Val Ala Arg
                205                 210                 215 tgc tgg tgc tac gag acc gca gtt gct gtt gga gtt gaa cct gat aac      724
Cys Trp Cys Tyr Glu Thr Ala Val Ala Val Gly Val Glu Pro Asp Asn
                220                 225                 230 aag ctg cct tac aat gat tac tat gag tac ttt ggc cct gat tat act      772
Lys Leu Pro Tyr Asn Asp Tyr Tyr Glu Tyr Phe Gly Pro Asp Tyr Thr
            235                 240                 245 ctt cat atc caa cca aaa agt gtt gaa aac ctg aat acc aca aag gac      820
Leu His Ile Gln Pro Lys Ser Val Glu Asn Leu Asn Thr Thr Lys Asp
        250                 255                 260 ttg gag aac ata aag aac atg ata ttg gag aac ctg tca aag ata gaa      868
Leu Glu Asn Ile Lys Asn Met Ile Leu Glu Asn Leu Ser Lys Ile Glu
265                 270                 275                 280 cat gtt ccc agc act caa ttc cat gac aga ccg tca gac cct gaa gct      916
His Val Pro Ser Thr Gln Phe His Asp Arg Pro Ser Asp Pro Glu Ala
```

-continued

| | | | | | | | | | | | | | | | |
|---|---|---|---|---|---|---|---|---|---|---|---|---|---|---|---|
| | | | | 285 | | | | 290 | | | | | 295 | | |
| cca | gag | gag | aaa | gag | gag | gac | atg | gac | aag | agg | cca | cct | cag | cgc | agc | 964 |
| Pro | Glu | Glu | Lys | Glu | Glu | Asp | Met | Asp | Lys | Arg | Pro | Pro | Gln | Arg | Ser | |
| | | | 300 | | | | | 305 | | | | | 310 | | |

| aga | tta | tgg | agc | gga | gga | gct | tac | gac | tct | gat | aca | gag | gat | cct | gac | 1012 |
| Arg | Leu | Trp | Ser | Gly | Gly | Ala | Tyr | Asp | Ser | Asp | Thr | Glu | Asp | Pro | Asp | |
| | | 315 | | | | | 320 | | | | | 325 | | | | |

| agc | ctg | aaa | agc | gag | ggt | aaa | gac | gta | act | gct | aac | ttc | cag | atg | aag | 1060 |
| Ser | Leu | Lys | Ser | Glu | Gly | Lys | Asp | Val | Thr | Ala | Asn | Phe | Gln | Met | Lys | |
| | 330 | | | | | 335 | | | | | 340 | | | | | |

| gat | gaa | cca | aaa | gat | gat | ctg | tag | aagtttcaga | agtgccccca | aagttactga | 1114 |
| Asp | Glu | Pro | Lys | Asp | Asp | Leu | | | | | |
| 345 | | | | 350 | | | | | | | | gttgtcaatg ggatcgtcga catgcatgtt gaagagtggg gacgcatctg aacctgtccg    1174 tgctgatatc tgccgctgtg catctgtaac agactgaacg ttttgctggt tccagctttc    1234 ctgcgtgttg gtaactagac tagatatatg gcccttggt gggtcccaaa ctgttgagct     1294 ggagaaatga agtgattatt ctcgcatgat ttactgtagc atgcatgtaa tcattaccca    1354 ttagttcatt aggctatcaa cagtagttta ctcatcccca tattcaaact tcactatgcg    1414 cgcatacagt gatttgagtg accatatgga taaactttga agatgaaaaa aaaaaaaaa     1474 a                                                                    1475

<210> SEQ ID NO 4
<211> LENGTH: 351
<212> TYPE: PRT
<213> ORGANISM: Zea mays

<400> SEQUENCE: 4

Met Ala Ala Ser Gly Glu Gly Ala Ser Leu Pro Ser Pro Ala Gly Gly
 1               5                  10                  15

Glu Asp Ala His Arg Arg Val Ser Tyr Phe Tyr Glu Pro Ser Ile
            20                  25                  30

Gly Asp Tyr Tyr Tyr Gly Gln Gly His Pro Met Lys Pro His His Ala
        35                  40                  45

Lys Lys Ser Glu Ala Ser Gly Phe Cys Tyr Val Asn Asp Ile Val Leu
    50                  55                  60

Ala Ile Leu Glu Leu Leu Lys Phe His Arg Arg Val Leu Tyr Val Asp
65                  70                  75                  80

Ile Asp Val His His Gly Asp Gly Val Glu Glu Ala Phe Phe Thr Thr
                85                  90                  95

Asn Arg Val Met Thr Val Ser Phe His Lys Tyr Gly Asp Phe Phe Pro
            100                 105                 110

Gly Thr Gly His Ile Thr Asp Val Gly Ala Ala Glu Gly Lys His Tyr
        115                 120                 125

Ala Leu Asn Val Pro Leu Ser Asp Gly Ile Asp Asp Thr Thr Phe Arg
    130                 135                 140

Gly Leu Phe Gln Cys Ile Ile Lys Lys Val Met Glu Val Tyr Gln Pro
145                 150                 155                 160

Asp Val Val Leu Gln Cys Gly Ala Asp Ser Leu Ala Gly Asp Arg
                165                 170                 175

Leu Gly Cys Phe Asn Leu Ser Val Lys Gly His Ala Asp Cys Leu Arg
            180                 185                 190

Phe Leu Arg Ser Tyr Asn Val Pro Met Met Val Leu Gly Gly Gly Gly
        195                 200                 205

-continued

```
Tyr Thr Ile Arg Asn Val Ala Arg Cys Trp Cys Tyr Glu Thr Ala Val
    210                 215                 220

Ala Val Gly Val Glu Pro Asp Asn Lys Leu Pro Tyr Asn Asp Tyr Tyr
225                 230                 235                 240

Glu Tyr Phe Gly Pro Asp Tyr Thr Leu His Ile Gln Pro Lys Ser Val
                245                 250                 255

Glu Asn Leu Asn Thr Thr Lys Asp Leu Glu Asn Ile Lys Asn Met Ile
            260                 265                 270

Leu Glu Asn Leu Ser Lys Ile Glu His Val Pro Ser Thr Gln Phe His
        275                 280                 285

Asp Arg Pro Ser Asp Pro Glu Ala Pro Glu Glu Lys Glu Asp Met
    290                 295                 300

Asp Lys Arg Pro Pro Gln Arg Ser Arg Leu Trp Ser Gly Gly Ala Tyr
305                 310                 315                 320

Asp Ser Asp Thr Glu Asp Pro Asp Ser Leu Lys Ser Glu Gly Lys Asp
                325                 330                 335

Val Thr Ala Asn Phe Gln Met Lys Asp Glu Pro Lys Asp Asp Leu
            340                 345                 350
```

<210> SEQ ID NO 5
<211> LENGTH: 2019
<212> TYPE: DNA
<213> ORGANISM: Zea mays
<220> FEATURE:
<221> NAME/KEY: CDS
<222> LOCATION: (140)..(1459)

<400> SEQUENCE: 5

```
ccacgcgtcc gagcgcctct cgcctctcgc cctacaggag gcaccctaca gaacccaacc      60
aaaaagcgcc ggcggcaaac agaacccaac ccaaagcgcc ggcggcaagc gaagagaaag     120
cgccggcact aatccgacg atg gac gcg tcg gcc ggc ggc ggc ggc aac tcc      172
                     Met Asp Ala Ser Ala Gly Gly Gly Gly Asn Ser
                      1               5                  10 ctg ccg acc act ggc gcg gac ggg tcg aag cgc cgc gtc tgc tac ttc       220
Leu Pro Thr Thr Gly Ala Asp Gly Ser Lys Arg Arg Val Cys Tyr Phe
            15                  20                  25 tac gac gcg gag gtg ggc aac tac tac tac ggg cag ggc cac ccg atg       268
Tyr Asp Ala Glu Val Gly Asn Tyr Tyr Tyr Gly Gln Gly His Pro Met
        30                  35                  40 aag ccg cac cgc atc cgc atg acc cac gcg ctc ctc ggc cgc tac ggc       316
Lys Pro His Arg Ile Arg Met Thr His Ala Leu Leu Gly Arg Tyr Gly
    45                  50                  55 ctc ctc gac cag atg caa gtg ttc cgc cct cac cct gcc cgc gac cgc       364
Leu Leu Asp Gln Met Gln Val Phe Arg Pro His Pro Ala Arg Asp Arg
60                  65                  70                  75 gac ctc tgc cgc ttc cac gcc gac gat tac gtc tcc ttc ctc cgg tcc       412
Asp Leu Cys Arg Phe His Ala Asp Asp Tyr Val Ser Phe Leu Arg Ser
                80                  85                  90 gtc acc ccc gaa acg cag cag gac cag atc cgc gcg ctc aag cgc ttc       460
Val Thr Pro Glu Thr Gln Gln Asp Gln Ile Arg Ala Leu Lys Arg Phe
            95                 100                 105 aac gtc ggc gag gac tgc ccc gtc ttc gac ggt ctc tac agt ttc tgt       508
Asn Val Gly Glu Asp Cys Pro Val Phe Asp Gly Leu Tyr Ser Phe Cys
        110                 115                 120 cag acg tac gcg ggg ggc tct gtt ggc ggc gcc gtc aag ctc aac cat       556
Gln Thr Tyr Ala Gly Gly Ser Val Gly Gly Ala Val Lys Leu Asn His
    125                 130                 135 ggc cat gat atc gcc atc aac tgg gcc ggc gga ctc cac cac gcc aag       604
```

```
Gly His Asp Ile Ala Ile Asn Trp Ala Gly Gly Leu His His Ala Lys
140                 145                 150                 155 aag tgc gag gcc tcc ggg ttt tgc tat gtt aat gac att gtc ctc gcc        652
Lys Cys Glu Ala Ser Gly Phe Cys Tyr Val Asn Asp Ile Val Leu Ala
                160                 165                 170 atc ctc gag ctc ctc aag tac cac cag cgc gtt ctg tac gtg gac att        700
Ile Leu Glu Leu Leu Lys Tyr His Gln Arg Val Leu Tyr Val Asp Ile
            175                 180                 185 gat atc cac cac ggg gac ggc gtg gag gag gct ttt tat acc aca gac        748
Asp Ile His His Gly Asp Gly Val Glu Glu Ala Phe Tyr Thr Thr Asp
        190                 195                 200 cgg gtg atg aca gtc tca ttc cac aag ttt gga gat tat ttc cct ggg        796
Arg Val Met Thr Val Ser Phe His Lys Phe Gly Asp Tyr Phe Pro Gly
    205                 210                 215 aca ggg gac att cgt gat gtt ggg cac tca aag ggt aaa tat tac tcc        844
Thr Gly Asp Ile Arg Asp Val Gly His Ser Lys Gly Lys Tyr Tyr Ser
220                 225                 230                 235 ctg aat gtt ccc ctg gac gat ggt att gat gat gag agc tac cag tcg        892
Leu Asn Val Pro Leu Asp Asp Gly Ile Asp Asp Glu Ser Tyr Gln Ser
                240                 245                 250 ttg ttc aag cca ata atg ggc aag gtg atg gag gtc ttc aac cct ggt        940
Leu Phe Lys Pro Ile Met Gly Lys Val Met Glu Val Phe Asn Pro Gly
            255                 260                 265 gca gtc gtg ctc cag tgt ggt gcg gat tca ttg tcg ggt gac agg ttg        988
Ala Val Val Leu Gln Cys Gly Ala Asp Ser Leu Ser Gly Asp Arg Leu
        270                 275                 280 ggc tgt ttc aac ctc tct att aag ggt cac gca gaa tgt gta aga ttt       1036
Gly Cys Phe Asn Leu Ser Ile Lys Gly His Ala Glu Cys Val Arg Phe
    285                 290                 295 atg agg tcc ttc aac gtc ccg ctg ttg ctg ctt ggt ggt ggt ggg tat       1084
Met Arg Ser Phe Asn Val Pro Leu Leu Leu Leu Gly Gly Gly Gly Tyr
300                 305                 310                 315 acc ata aga aac gtt gca cgg tgt tgg tgc tac gag aca gga gtt gcc       1132
Thr Ile Arg Asn Val Ala Arg Cys Trp Cys Tyr Glu Thr Gly Val Ala
                320                 325                 330 ctt ggt cat gag ctc act gac aag atg cca cct aat gag tac tat gag       1180
Leu Gly His Glu Leu Thr Asp Lys Met Pro Pro Asn Glu Tyr Tyr Glu
            335                 340                 345 tat ttt ggt cca gat tac act cta cat gtc gct cca agt aac atg gag       1228
Tyr Phe Gly Pro Asp Tyr Thr Leu His Val Ala Pro Ser Asn Met Glu
        350                 355                 360 aat aaa aac aca cgg cat caa ttg gat gac ata aaa tca aaa ctt cta       1276
Asn Lys Asn Thr Arg His Gln Leu Asp Asp Ile Lys Ser Lys Leu Leu
    365                 370                 375 gat aat ctt tca aaa ctc cga cat gct cct agt gtt cag ttt caa gag       1324
Asp Asn Leu Ser Lys Leu Arg His Ala Pro Ser Val Gln Phe Gln Glu
380                 385                 390                 395 cga cct cct gag gct gag tta cct gag caa gat gaa gac aaa gag aat       1372
Arg Pro Pro Glu Ala Glu Leu Pro Glu Gln Asp Glu Asp Lys Glu Asn
                400                 405                 410 cct gat gaa aga cat gat gct gat tct gat gtg gag atg aat gat gcc       1420
Pro Asp Glu Arg His Asp Ala Asp Ser Asp Val Glu Met Asn Asp Ala
            415                 420                 425 aaa cct ttg cag gac tct gga agg atg tca ata gtg tag ctgcagaaca        1469
Lys Pro Leu Gln Asp Ser Gly Arg Met Ser Ile Val
        430                 435                 440 ttctagaggc actggacctg tggctgatgg agttggttcc tcgaaacaaa cctttccgaa     1529
tgccactagt cgaatggcca tagatgaacc aaacgctctt gagagttgag caagagggtt    1589
```

-continued

```
caaacaaatt gcaggaccaa ccatcgatgc acctcaagta gctaatgtca tctgtagcct    1649
gtcgattctt ttgcgcaaat tcattaactg taggcaagcc atgcgtggac tgaagcaggg    1709
agcagaagca agtgctcgac caagaagttg tgcatctgaa atctatattt tttgcgcgtc    1769
atatttgtat taccgacagt tgcaaacgat ggtttatcat gaaaaatttg tctttccacc    1829
cttggcttct gcagtggaag gggttgatat cgtagtatgc atcaattatg cattttgtcc    1889
attccccatc cccaaatgag aagtgggtag tccccgacgg gttttgaatg gccaacagtt    1949
ttaagggagg gaagcagccc ggaggccaaa aaaaaagcaa cgagatgtac ggcaaaaaaa    2009
aaaaaaaaaa                                                          2019
```

<210> SEQ ID NO 6
<211> LENGTH: 439
<212> TYPE: PRT
<213> ORGANISM: Zea mays

<400> SEQUENCE: 6

```
Met Asp Ala Ser Ala Gly Gly Gly Asn Ser Leu Pro Thr Thr Gly
  1               5                  10                  15

Ala Asp Gly Ser Lys Arg Arg Val Cys Tyr Phe Tyr Asp Ala Glu Val
                 20                  25                  30

Gly Asn Tyr Tyr Tyr Gly Gln Gly His Pro Met Lys Pro His Arg Ile
             35                  40                  45

Arg Met Thr His Ala Leu Leu Gly Arg Tyr Gly Leu Leu Asp Gln Met
         50                  55                  60

Gln Val Phe Arg Pro His Pro Ala Arg Asp Arg Asp Leu Cys Arg Phe
     65                  70                  75                  80

His Ala Asp Asp Tyr Val Ser Phe Leu Arg Ser Val Thr Pro Glu Thr
                 85                  90                  95

Gln Gln Asp Gln Ile Arg Ala Leu Lys Arg Phe Asn Val Gly Glu Asp
            100                 105                 110

Cys Pro Val Phe Asp Gly Leu Tyr Ser Phe Cys Gln Thr Tyr Ala Gly
        115                 120                 125

Gly Ser Val Gly Gly Ala Val Lys Leu Asn His Gly His Asp Ile Ala
    130                 135                 140

Ile Asn Trp Ala Gly Gly Leu His His Ala Lys Lys Cys Glu Ala Ser
145                 150                 155                 160

Gly Phe Cys Tyr Val Asn Asp Ile Val Leu Ala Ile Leu Glu Leu Leu
                165                 170                 175

Lys Tyr His Gln Arg Val Leu Tyr Val Asp Ile Asp Ile His His Gly
            180                 185                 190

Asp Gly Val Glu Glu Ala Phe Tyr Thr Thr Asp Arg Val Met Thr Val
        195                 200                 205

Ser Phe His Lys Phe Gly Asp Tyr Phe Pro Gly Thr Gly Asp Ile Arg
    210                 215                 220

Asp Val Gly His Ser Lys Gly Lys Tyr Tyr Ser Leu Asn Val Pro Leu
225                 230                 235                 240

Asp Asp Gly Ile Asp Asp Glu Ser Tyr Gln Ser Leu Phe Lys Pro Ile
                245                 250                 255

Met Gly Lys Val Met Glu Val Phe Asn Pro Gly Ala Val Val Leu Gln
            260                 265                 270

Cys Gly Ala Asp Ser Leu Ser Gly Asp Arg Leu Gly Cys Phe Asn Leu
        275                 280                 285

Ser Ile Lys Gly His Ala Glu Cys Val Arg Phe Met Arg Ser Phe Asn
```

-continued

```
                        290                 295                 300
Val Pro Leu Leu Leu Gly Gly Gly Tyr Thr Ile Arg Asn Val
305                 310                 315                 320

Ala Arg Cys Trp Cys Tyr Glu Thr Gly Val Ala Leu Gly His Glu Leu
                325                 330                 335

Thr Asp Lys Met Pro Pro Asn Glu Tyr Tyr Glu Tyr Phe Gly Pro Asp
                340                 345                 350

Tyr Thr Leu His Val Ala Pro Ser Asn Met Glu Asn Lys Asn Thr Arg
                355                 360                 365

His Gln Leu Asp Asp Ile Lys Ser Lys Leu Leu Asp Asn Leu Ser Lys
            370                 375                 380

Leu Arg His Ala Pro Ser Val Gln Phe Gln Arg Pro Pro Glu Ala
385                 390                 395                 400

Glu Leu Pro Glu Gln Asp Glu Asp Lys Glu Asn Pro Asp Glu Arg His
                405                 410                 415

Asp Ala Asp Ser Asp Val Glu Met Asn Asp Ala Lys Pro Leu Gln Asp
                420                 425                 430

Ser Gly Arg Met Ser Ile Val
            435

<210> SEQ ID NO 7
<211> LENGTH: 1943
<212> TYPE: DNA
<213> ORGANISM: Zea mays
<220> FEATURE:
<221> NAME/KEY: CDS
<222> LOCATION: (57)..(1610)

<400> SEQUENCE: 7
ccacgcgtcc gagagataac acacacacac acaaacccca atcccctgcg gcggcg atg        59
                                                                  Met
                                                                    1 gac ccg tca tcg gcg ggc tcc ggc ggc aac tcc ctc ccg tcc gtc ggc         107
Asp Pro Ser Ser Ala Gly Ser Gly Gly Asn Ser Leu Pro Ser Val Gly
            5                  10                  15 ccc gac ggg cag aag cgg cgc gtg tgc tac ttc tac gac ccg gat gtg         155
Pro Asp Gly Gln Lys Arg Arg Val Cys Tyr Phe Tyr Asp Pro Asp Val
        20                  25                  30 ggc aac tac tac tac ggg cag ggc cat ccg atg aag ccg cac cgc atc         203
Gly Asn Tyr Tyr Tyr Gly Gln Gly His Pro Met Lys Pro His Arg Ile
    35                  40                  45 cgg atg acg cac tcg ctg ctg gcg cgc tac ggc ctc ctc aac cag atg         251
Arg Met Thr His Ser Leu Leu Ala Arg Tyr Gly Leu Leu Asn Gln Met
50                  55                  60                  65 cag gtg tac cgc ccc aac ccg gcc cgc gac cgc gac ctc tgc cgc ttc         299
Gln Val Tyr Arg Pro Asn Pro Ala Arg Asp Arg Asp Leu Cys Arg Phe
                70                  75                  80 cac gcc gac gac tac atc aac ttc ctg cgc tcc gtc acg ccg gaa acg         347
His Ala Asp Asp Tyr Ile Asn Phe Leu Arg Ser Val Thr Pro Glu Thr
            85                  90                  95 cag cag gac cag atc cgc ctg ctc aag cgc ttc aac gtc ggc gag gac         395
Gln Gln Asp Gln Ile Arg Leu Leu Lys Arg Phe Asn Val Gly Glu Asp
        100                 105                 110 tgc ccc gtc ttc gac ggc ctc tac agc ttc tgc cag acc tat gcg ggc         443
Cys Pro Val Phe Asp Gly Leu Tyr Ser Phe Cys Gln Thr Tyr Ala Gly
    115                 120                 125 gcc tcc gtc ggc ggg gcc gtc aag ctc aac cac ggc cat gac atc gca         491
Ala Ser Val Gly Gly Ala Val Lys Leu Asn His Gly His Asp Ile Ala
130                 135                 140                 145
```

```
atc aac tgg tcg ggg ggc ctg cac cac gcc aag aag tgc gag gcg tcg     539
Ile Asn Trp Ser Gly Gly Leu His His Ala Lys Lys Cys Glu Ala Ser
            150                 155                 160 ggc ttc tgc tac gtc aat gac atc gtg ctc gcc ata ctc gag ctg ctc     587
Gly Phe Cys Tyr Val Asn Asp Ile Val Leu Ala Ile Leu Glu Leu Leu
        165                 170                 175 aag cat cac gag aga gtt ctg tat gtc gat atc gat atc cac cat ggt     635
Lys His His Glu Arg Val Leu Tyr Val Asp Ile Asp Ile His His Gly
        180                 185                 190 gat gga gtg gag gag gct ttc tac aca aca gat agg gtt atg act gtc     683
Asp Gly Val Glu Glu Ala Phe Tyr Thr Thr Asp Arg Val Met Thr Val
    195                 200                 205 tcg ttc cac aag ttt ggt gat tat ttc cca gga aca ggg gat atc cgt     731
Ser Phe His Lys Phe Gly Asp Tyr Phe Pro Gly Thr Gly Asp Ile Arg
210                 215                 220                 225 gac att ggg cac tca aaa ggg aag tac tac tcc ctg aat gtc cct cta     779
Asp Ile Gly His Ser Lys Gly Lys Tyr Tyr Ser Leu Asn Val Pro Leu
                230                 235                 240 gat gat ggg att gat gat gaa agc tac cag tcc ctt ttt aag cca atc     827
Asp Asp Gly Ile Asp Asp Glu Ser Tyr Gln Ser Leu Phe Lys Pro Ile
            245                 250                 255 atg ggc aaa gtt atg gag gtt ttc cgc cct ggt gca gtt gtg ctt cag     875
Met Gly Lys Val Met Glu Val Phe Arg Pro Gly Ala Val Val Leu Gln
        260                 265                 270 tgt ggt gct gat tcc ttg tct ggg gat agg ttg ggc tgc ttc aac ctc     923
Cys Gly Ala Asp Ser Leu Ser Gly Asp Arg Leu Gly Cys Phe Asn Leu
    275                 280                 285 tca atc aaa ggt cat gcg gaa tgt gtt agg tat atg agg tct ttc aac     971
Ser Ile Lys Gly His Ala Glu Cys Val Arg Tyr Met Arg Ser Phe Asn
290                 295                 300                 305 gtt cca ttg ttg ctc ctt ggt ggt ggt gga tat acc ata aga aat gtt    1019
Val Pro Leu Leu Leu Leu Gly Gly Gly Gly Tyr Thr Ile Arg Asn Val
                310                 315                 320 gca cgc tgt tgg tgt tat gag act gga gtt gct ctt ggc caa gag cct    1067
Ala Arg Cys Trp Cys Tyr Glu Thr Gly Val Ala Leu Gly Gln Glu Pro
            325                 330                 335 gaa gac aag atg cct gtt aat gag tac tat gaa tac ttc ggt cca gat    1115
Glu Asp Lys Met Pro Val Asn Glu Tyr Tyr Glu Tyr Phe Gly Pro Asp
        340                 345                 350 tac act ctt cat gtt gca cca agt aac atg gag aac aaa aat aca cga    1163
Tyr Thr Leu His Val Ala Pro Ser Asn Met Glu Asn Lys Asn Thr Arg
    355                 360                 365 caa caa ctg gat gat ata cga tct aaa ctt ctg gat aat ctt tca aaa    1211
Gln Gln Leu Asp Asp Ile Arg Ser Lys Leu Leu Asp Asn Leu Ser Lys
370                 375                 380                 385 ctt cga cat gct cct agt gtc cac ttt caa gag aga gtt cct gac aca    1259
Leu Arg His Ala Pro Ser Val His Phe Gln Glu Arg Val Pro Asp Thr
                390                 395                 400 gaa ata cct gag caa gat gaa gat caa gat gat cca gat gaa cga cat    1307
Glu Ile Pro Glu Gln Asp Glu Asp Gln Asp Asp Pro Asp Glu Arg His
            405                 410                 415 gat cct gac tct gat atg gaa gtg gat gac cac aag gct gtg gaa gag    1355
Asp Pro Asp Ser Asp Met Glu Val Asp Asp His Lys Ala Val Glu Glu
        420                 425                 430 tca tcg agg agg agc att cta ggt ata aaa atc aag aga gaa ttt ggt    1403
Ser Ser Arg Arg Ser Ile Leu Gly Ile Lys Ile Lys Arg Glu Phe Gly
    435                 440                 445 gaa aat gcg acc aga gta cag gat ggt ggc agg gtt gca tct gaa cat    1451
Glu Asn Ala Thr Arg Val Gln Asp Gly Gly Arg Val Ala Ser Glu His
```

```
              450            455            460            465
aga gga ctg gaa ccc atg gca gaa gac att ggt tcc tcc aag caa gct   1499
Arg Gly Leu Glu Pro Met Ala Glu Asp Ile Gly Ser Ser Lys Gln Ala
                470            475            480 cct cag gca gat gcc agt gca atg gcc atc gat gaa cca agc aat gtc   1547
Pro Gln Ala Asp Ala Ser Ala Met Ala Ile Asp Glu Pro Ser Asn Val
            485            490            495 aag aat gaa cct gag agc tca act aaa ttg caa ggc caa gca gct gcg   1595
Lys Asn Glu Pro Glu Ser Ser Thr Lys Leu Gln Gly Gln Ala Ala Ala
        500            505            510 tac cac aag cca tag ctgcgaccat caagagttgc tgggtttctg ctaggcaact   1650
Tyr His Lys Pro
    515 tcctgcttga tttggacagt ccagaaaaca gaagtgaatc cgcaatacgt ccctgccatt   1710 tcaaatttga cttggttaca cctatctgtg acaatgttaa tgtaatgaga tcccatggca   1770 ctagtgaagt tcccaggtgt ccacctggga ttgcttgcgg ttgagagaga cgatagtctg   1830 atgacccatg tatacatgaa gcccatgatc tcagttgtac agtcattagc caatacaaat   1890 atgcagtgga ctaaagggtg attcattgcg tgttcttaaa aaaaaaaaaa aaa          1943

<210> SEQ ID NO 8
<211> LENGTH: 517
<212> TYPE: PRT
<213> ORGANISM: Zea mays

<400> SEQUENCE: 8

Met Asp Pro Ser Ser Ala Gly Ser Gly Gly Asn Ser Leu Pro Ser Val
 1               5                  10                  15

Gly Pro Asp Gly Gln Lys Arg Val Cys Tyr Phe Tyr Asp Pro Asp
             20                  25                  30

Val Gly Asn Tyr Tyr Gly Gln Gly His Pro Met Lys Pro His Arg
         35                  40                  45

Ile Arg Met Thr His Ser Leu Leu Ala Arg Tyr Gly Leu Leu Asn Gln
     50                  55                  60

Met Gln Val Tyr Arg Pro Asn Pro Ala Arg Asp Arg Asp Leu Cys Arg
 65                  70                  75                  80

Phe His Ala Asp Asp Tyr Ile Asn Phe Leu Arg Ser Val Thr Pro Glu
                 85                  90                  95

Thr Gln Gln Asp Gln Ile Arg Leu Leu Lys Arg Phe Asn Val Gly Glu
            100                 105                 110

Asp Cys Pro Val Phe Asp Gly Leu Tyr Ser Phe Cys Gln Thr Tyr Ala
        115                 120                 125

Gly Ala Ser Val Gly Gly Ala Val Lys Leu Asn His Gly His Asp Ile
    130                 135                 140

Ala Ile Asn Trp Ser Gly Gly Leu His His Ala Lys Lys Cys Glu Ala
145                 150                 155                 160

Ser Gly Phe Cys Tyr Val Asn Asp Ile Val Leu Ala Ile Leu Glu Leu
                165                 170                 175

Leu Lys His His Glu Arg Val Leu Tyr Val Asp Ile Asp Ile His His
            180                 185                 190

Gly Asp Gly Val Glu Glu Ala Phe Tyr Thr Thr Asp Arg Val Met Thr
        195                 200                 205

Val Ser Phe His Lys Phe Gly Asp Tyr Phe Pro Gly Thr Gly Asp Ile
    210                 215                 220

Arg Asp Ile Gly His Ser Lys Gly Lys Tyr Tyr Ser Leu Asn Val Pro
```

```
                225                 230                 235                 240
Leu Asp Asp Gly Ile Asp Asp Glu Ser Tyr Gln Ser Leu Phe Lys Pro
                245                 250                 255

Ile Met Gly Lys Val Met Glu Val Phe Arg Pro Gly Ala Val Val Leu
            260                 265                 270

Gln Cys Gly Ala Asp Ser Leu Ser Gly Asp Arg Leu Gly Cys Phe Asn
        275                 280                 285

Leu Ser Ile Lys Gly His Ala Glu Cys Val Arg Tyr Met Arg Ser Phe
    290                 295                 300

Asn Val Pro Leu Leu Leu Gly Gly Gly Tyr Thr Ile Arg Asn
305                 310                 315                 320

Val Ala Arg Cys Trp Cys Tyr Glu Thr Gly Val Ala Leu Gly Gln Glu
                325                 330                 335

Pro Glu Asp Lys Met Pro Val Asn Glu Tyr Tyr Glu Tyr Phe Gly Pro
            340                 345                 350

Asp Tyr Thr Leu His Val Ala Pro Ser Asn Met Glu Asn Lys Asn Thr
        355                 360                 365

Arg Gln Gln Leu Asp Asp Ile Arg Ser Lys Leu Leu Asp Asn Leu Ser
    370                 375                 380

Lys Leu Arg His Ala Pro Ser Val His Phe Gln Glu Arg Val Pro Asp
385                 390                 395                 400

Thr Glu Ile Pro Glu Gln Asp Glu Asp Gln Asp Asp Pro Asp Glu Arg
                405                 410                 415

His Asp Pro Asp Ser Asp Met Glu Val Asp Asp His Lys Ala Val Glu
            420                 425                 430

Glu Ser Ser Arg Arg Ser Ile Leu Gly Ile Lys Ile Lys Arg Glu Phe
        435                 440                 445

Gly Glu Asn Ala Thr Arg Val Gln Asp Gly Gly Arg Val Ala Ser Glu
    450                 455                 460

His Arg Gly Leu Glu Pro Met Ala Glu Asp Ile Gly Ser Ser Lys Gln
465                 470                 475                 480

Ala Pro Gln Ala Asp Ala Ser Ala Met Ala Ile Asp Glu Pro Ser Asn
                485                 490                 495

Val Lys Asn Glu Pro Glu Ser Ser Thr Lys Leu Gln Gly Gln Ala Ala
            500                 505                 510

Ala Tyr His Lys Pro
        515

<210> SEQ ID NO 9
<211> LENGTH: 1576
<212> TYPE: DNA
<213> ORGANISM: Zea mays
<220> FEATURE:
<221> NAME/KEY: CDS
<222> LOCATION: (38)..(1336)

<400> SEQUENCE: 9
agctcctgct gtctttcaaa taataaagtt cgaattt atg att gct agc tta cca       55
                                        Met Ile Ala Ser Leu Pro
                                          1               5 att tat ttt atc aca ccc att gta gga gat gtt ggc aat gtc tac ttt      103
Ile Tyr Phe Ile Thr Pro Ile Val Gly Asp Val Gly Asn Val Tyr Phe
             10                  15                  20 ggg cca aat cac ccc atg aag cca cat cgt ctc tgt atg aca cat cac      151
Gly Pro Asn His Pro Met Lys Pro His Arg Leu Cys Met Thr His His
         25                  30                  35
```

-continued

| | | |
|---|---|---|
| ctt gtt ctt tca tat gga ctt cat caa aag atg gag ata tat agg cca<br>Leu Val Leu Ser Tyr Gly Leu His Gln Lys Met Glu Ile Tyr Arg Pro<br>40           45                  50 | | 199 |
| cac aaa gca tat cca ata gag ctt gcc caa ttc cat tct gct gat tat<br>His Lys Ala Tyr Pro Ile Glu Leu Ala Gln Phe His Ser Ala Asp Tyr<br>55               60               65               70 | | 247 |
| gtg gaa ttc ttg cac cgg ata act cct gat tcc cag cac cta tat gca<br>Val Glu Phe Leu His Arg Ile Thr Pro Asp Ser Gln His Leu Tyr Ala<br>       75                  80              85 | | 295 |
| agt gaa cta act aga tac aat ctt gga gaa gac tgt ccg gtc ttt gat<br>Ser Glu Leu Thr Arg Tyr Asn Leu Gly Glu Asp Cys Pro Val Phe Asp<br>             90              95                 100 | | 343 |
| aat ttg ttt gag ttc tgc caa atc tat gcg gga gga act tta gat gct<br>Asn Leu Phe Glu Phe Cys Gln Ile Tyr Ala Gly Gly Thr Leu Asp Ala<br>         105             110              115 | | 391 |
| gct cgc aga tta aat cat aaa ata tgt gac att gcc att aat tgg gct<br>Ala Arg Arg Leu Asn His Lys Ile Cys Asp Ile Ala Ile Asn Trp Ala<br>120              125              130 | | 439 |
| ggt ggg cta cat cat gcc aaa aag tgt gag gct tca ggc ttc tgt tac<br>Gly Gly Leu His His Ala Lys Lys Cys Glu Ala Ser Gly Phe Cys Tyr<br>135              140              145              150 | | 487 |
| att aat gat cta gta tta gga att ctg gag ctt ctc aag tac cat gcc<br>Ile Asn Asp Leu Val Leu Gly Ile Leu Glu Leu Leu Lys Tyr His Ala<br>              155              160              165 | | 535 |
| agg gtt ctt tat att gac att gat gtc cat cat gga gat gga gtt gaa<br>Arg Val Leu Tyr Ile Asp Ile Asp Val His His Gly Asp Gly Val Glu<br>         170              175              180 | | 583 |
| gaa gcc ttt tat ttc act gac agg gta atg act gtg agt ttc cac aag<br>Glu Ala Phe Tyr Phe Thr Asp Arg Val Met Thr Val Ser Phe His Lys<br>     185               190              195 | | 631 |
| tat ggt gac ctg ttc ttt cct gga aca ggt gat att aag gat ata gga<br>Tyr Gly Asp Leu Phe Phe Pro Gly Thr Gly Asp Ile Lys Asp Ile Gly<br>200              205              210 | | 679 |
| gaa agg gaa gga aaa tat tat gct atc aac att cca ctt aaa gat ggg<br>Glu Arg Glu Gly Lys Tyr Tyr Ala Ile Asn Ile Pro Leu Lys Asp Gly<br>215              220              225              230 | | 727 |
| ata gat gac act agc ttt act cgg cct ttt aaa aca att att gcc aaa<br>Ile Asp Asp Thr Ser Phe Thr Arg Pro Phe Lys Thr Ile Ile Ala Lys<br>              235              240              245 | | 775 |
| gtt gtt gag aca tat ctg cct ggt gct att gtt ctt caa tgt ggg gct<br>Val Val Glu Thr Tyr Leu Pro Gly Ala Ile Val Leu Gln Cys Gly Ala<br>         250              255              260 | | 823 |
| gat tca ttg gcg agg gat cgt tta ggc tgc ttc aat ctc tct att gaa<br>Asp Ser Leu Ala Arg Asp Arg Leu Gly Cys Phe Asn Leu Ser Ile Glu<br>     265              270              275 | | 871 |
| ggc cat gct gaa tgt gta aag ttt gtc aag aaa ttc aat att ccc ctt<br>Gly His Ala Glu Cys Val Lys Phe Val Lys Lys Phe Asn Ile Pro Leu<br>280              285              290 | | 919 |
| ctg gta act gga ggt ggt gga tac acc aag gag aat gta gca cgg tgt<br>Leu Val Thr Gly Gly Gly Gly Tyr Thr Lys Glu Asn Val Ala Arg Cys<br>295              300              305              310 | | 967 |
| tgg gct gtt gaa act ggg gtc ctt tta gac aca gaa ctc cca aat gag<br>Trp Ala Val Glu Thr Gly Val Leu Leu Asp Thr Glu Leu Pro Asn Glu<br>              315              320              325 | | 1015 |
| att cca aaa aat gaa tat att gag tac ttt gct cca gat tat aca ttg<br>Ile Pro Lys Asn Glu Tyr Ile Glu Tyr Phe Ala Pro Asp Tyr Thr Leu<br>         330              335              340 | | 1063 |
| aaa gtt cca aat ttg aac atg gac aat ttg aac agt aag acc tat ctc<br>Lys Val Pro Asn Leu Asn Met Asp Asn Leu Asn Ser Lys Thr Tyr Leu<br>     345              350              355 | | 1111 |

-continued

```
agt tca atc aaa gtg caa gtg atg gag agt ttg cgg tac ata cag cat    1159
Ser Ser Ile Lys Val Gln Val Met Glu Ser Leu Arg Tyr Ile Gln His
    360             365                 370 gct cct ggt gtt caa atg caa gag gtt cct ccc gat ttt tat atc ccg    1207
Ala Pro Gly Val Gln Met Gln Glu Val Pro Pro Asp Phe Tyr Ile Pro
375             380                 385                 390 gac ttt gat gaa gat gaa ttg gat cct gat gaa cgt gtt gac cag cac    1255
Asp Phe Asp Glu Asp Glu Leu Asp Pro Asp Glu Arg Val Asp Gln His
            395                 400                 405 act caa gac aag cag att cac cgt gat gat gag tac tat gaa ggt gac    1303
Thr Gln Asp Lys Gln Ile His Arg Asp Asp Glu Tyr Tyr Glu Gly Asp
        410                 415                 420 aat gac aac gat cac gac gac ggc aca cgc taa tctgcttctt ctgaggccct  1356
Asn Asp Asn Asp His Asp Asp Gly Thr Arg
    425                 430 ggtgtaaatg gaaacctgag attcttcact gttgtgtgta gttcagcagc cttgagatgt  1416
aatagtttgt cagttgacag cagggatcta atttagcagg tcaaagtggt ttagactttt  1476
ataagggatt ctgacccctc ctgaattaca cattgtagta caagtctgca tattttaag   1536 catgcaaaaa ttcaaatttc tcaaaaaaaa aaaaaaaaa                         1576
```

<210> SEQ ID NO 10
<211> LENGTH: 432
<212> TYPE: PRT
<213> ORGANISM: Zea mays

<400> SEQUENCE: 10

```
Met Ile Ala Ser Leu Pro Ile Tyr Phe Ile Thr Pro Ile Val Gly Asp
 1               5                  10                  15

Val Gly Asn Val Tyr Phe Gly Pro Asn His Pro Met Lys Pro His Arg
            20                  25                  30

Leu Cys Met Thr His His Leu Val Leu Ser Tyr Gly Leu His Gln Lys
        35                  40                  45

Met Glu Ile Tyr Arg Pro His Lys Ala Tyr Pro Ile Glu Leu Ala Gln
    50                  55                  60

Phe His Ser Ala Asp Tyr Val Glu Phe Leu His Arg Ile Thr Pro Asp
65                  70                  75                  80

Ser Gln His Leu Tyr Ala Ser Glu Leu Thr Arg Tyr Asn Leu Gly Glu
                85                  90                  95

Asp Cys Pro Val Phe Asp Asn Leu Phe Glu Phe Cys Gln Ile Tyr Ala
            100                 105                 110

Gly Gly Thr Leu Asp Ala Ala Arg Arg Leu Asn His Lys Ile Cys Asp
        115                 120                 125

Ile Ala Ile Asn Trp Ala Gly Gly Leu His His Ala Lys Lys Cys Glu
    130                 135                 140

Ala Ser Gly Phe Cys Tyr Ile Asn Asp Leu Val Leu Gly Ile Leu Glu
145                 150                 155                 160

Leu Leu Lys Tyr His Ala Arg Val Leu Tyr Ile Asp Ile Asp Val His
                165                 170                 175

His Gly Asp Gly Val Glu Glu Ala Phe Tyr Phe Thr Asp Arg Val Met
            180                 185                 190

Thr Val Ser Phe His Lys Tyr Gly Asp Leu Phe Phe Pro Gly Thr Gly
        195                 200                 205

Asp Ile Lys Asp Ile Gly Glu Arg Glu Gly Lys Tyr Tyr Ala Ile Asn
    210                 215                 220
```

-continued

```
Ile Pro Leu Lys Asp Gly Ile Asp Asp Thr Ser Phe Thr Arg Pro Phe
225                 230                 235                 240

Lys Thr Ile Ile Ala Lys Val Val Glu Thr Tyr Leu Pro Gly Ala Ile
                245                 250                 255

Val Leu Gln Cys Gly Ala Asp Ser Leu Ala Arg Asp Arg Leu Gly Cys
            260                 265                 270

Phe Asn Leu Ser Ile Glu Gly His Ala Glu Cys Val Lys Phe Val Lys
        275                 280                 285

Lys Phe Asn Ile Pro Leu Leu Val Thr Gly Gly Gly Tyr Thr Lys
290                 295                 300

Glu Asn Val Ala Arg Cys Trp Ala Val Glu Thr Gly Val Leu Leu Asp
305                 310                 315                 320

Thr Glu Leu Pro Asn Glu Ile Pro Lys Asn Glu Tyr Ile Glu Tyr Phe
                325                 330                 335

Ala Pro Asp Tyr Thr Leu Lys Val Pro Asn Leu Asn Met Asp Asn Leu
            340                 345                 350

Asn Ser Lys Thr Tyr Leu Ser Ser Ile Lys Val Gln Val Met Glu Ser
        355                 360                 365

Leu Arg Tyr Ile Gln His Ala Pro Gly Val Gln Met Gln Glu Val Pro
370                 375                 380

Pro Asp Phe Tyr Ile Pro Asp Phe Asp Glu Asp Glu Leu Asp Pro Asp
385                 390                 395                 400

Glu Arg Val Asp Gln His Thr Gln Asp Lys Gln Ile His Arg Asp Asp
                405                 410                 415

Glu Tyr Tyr Glu Gly Asp Asn Asp Asn Asp His Asp Asp Gly Thr Arg
            420                 425                 430

<210> SEQ ID NO 11
<211> LENGTH: 1283
<212> TYPE: DNA
<213> ORGANISM: Zea mays
<220> FEATURE:
<221> NAME/KEY: CDS
<222> LOCATION: (79)..(996)

<400> SEQUENCE: 11
gttcccgtcc tgtccttcca cccggcggct taaaccctag ttctcactcc catcgccgct      60
tcagctccgc cgctgcag atg gag ttc tgg ggt ctc gag gtc aag cct ggt     111
                    Met Glu Phe Trp Gly Leu Glu Val Lys Pro Gly
                      1               5                  10 tcc act gtt aag tgt gag cct gga tat ggc ttt gtg ctg cac ctt tcc     159
Ser Thr Val Lys Cys Glu Pro Gly Tyr Gly Phe Val Leu His Leu Ser
            15                  20                  25 cag gct gct ctt ggg gaa tcg aag aag agt gat aat gcc ttg atg tat     207
Gln Ala Ala Leu Gly Glu Ser Lys Lys Ser Asp Asn Ala Leu Met Tyr
        30                  35                  40 gtc aaa att gat gat cag aaa ctt gcc att gga acc ctc tct gtt gac     255
Val Lys Ile Asp Asp Gln Lys Leu Ala Ile Gly Thr Leu Ser Val Asp
    45                  50                  55 aag aac cca cac ata caa ttt gat ctg att ttc gat aaa gag ttt gag     303
Lys Asn Pro His Ile Gln Phe Asp Leu Ile Phe Asp Lys Glu Phe Glu
60                  65                  70                  75 ctg tcg cac aca tca aaa act acc agc gtt ttc ttc act ggc tac aag     351
Leu Ser His Thr Ser Lys Thr Thr Ser Val Phe Phe Thr Gly Tyr Lys
                80                  85                  90 gtt gag cag cca ttc gag gaa gat gaa atg gat ctt gat tct gaa gat     399
Val Glu Gln Pro Phe Glu Glu Asp Glu Met Asp Leu Asp Ser Glu Asp
            95                  100                 105
```

```
gaa gac gag gag ctg aat gtt cca gta gtc aag gaa aat ggc aaa gct       447
Glu Asp Glu Glu Leu Asn Val Pro Val Val Lys Glu Asn Gly Lys Ala
            110                 115                 120 gat gag aag aaa cag aaa agt caa gaa aag gca gtt gct gca cct tca       495
Asp Glu Lys Lys Gln Lys Ser Gln Glu Lys Ala Val Ala Ala Pro Ser
        125                 130                 135 aaa tca agt ccg gat tcc aag aag agc aag gat gac gac gat tct gat       543
Lys Ser Ser Pro Asp Ser Lys Lys Ser Lys Asp Asp Asp Asp Ser Asp
140                 145                 150                 155 gag gac gag act gat gat tct gat gag gat gag acg gac gat tct gat       591
Glu Asp Glu Thr Asp Asp Ser Asp Glu Asp Glu Thr Asp Asp Ser Asp
                160                 165                 170 gag ggt ttg tct cct gaa gaa ggc gat gat gat tca agt gat gaa gat       639
Glu Gly Leu Ser Pro Glu Glu Gly Asp Asp Asp Ser Ser Asp Glu Asp
            175                 180                 185 gat acc agt gac gat gag gag gaa gac act cca act cct aag aag cct       687
Asp Thr Ser Asp Asp Glu Glu Asp Thr Pro Thr Pro Lys Lys Pro
        190                 195                 200 gag gta ggc aag aag aga gct gct gaa agt tcc gtg ctg aaa act cct       735
Glu Val Gly Lys Lys Arg Ala Ala Glu Ser Ser Val Leu Lys Thr Pro
205                 210                 215 cta tct gat aag aaa gca aag gtt gcc aca ccg tca tct cag aag aca       783
Leu Ser Asp Lys Lys Ala Lys Val Ala Thr Pro Ser Ser Gln Lys Thr
220                 225                 230                 235 ggt ggc aag aag ggc gcc gcg gtc cat gtg gca act cca cac cca gca       831
Gly Gly Lys Lys Gly Ala Ala Val His Val Ala Thr Pro His Pro Ala
                240                 245                 250 aaa ggc aag acc att gta aac aat gac aaa tcg gtc aag tct cca aaa       879
Lys Gly Lys Thr Ile Val Asn Asn Asp Lys Ser Val Lys Ser Pro Lys
            255                 260                 265 tct gcg cca aaa tct ggt gtc cct tgc aaa tcg tgc agc aag tca ttc       927
Ser Ala Pro Lys Ser Gly Val Pro Cys Lys Ser Cys Ser Lys Ser Phe
        270                 275                 280 atc agt gag acg gca ctt cag gct cac tcg aag gcg aac atg ggg gca       975
Ile Ser Glu Thr Ala Leu Gln Ala His Ser Lys Ala Asn Met Gly Ala
285                 290                 295 agt gag tcg cag gtc caa tag agtcaacaac aaatgcgaaa catgggagag         1026
Ser Glu Ser Gln Val Gln
300                 305 gagggtaagc gagagtctcg aaagagtgtc ggtggaagta ggcctacctt attttgttta    1086
gagacgggct atgcgttcga tgtagcaaaa caaggctgtg gtttgtgtac ttcaatattt    1146
gggttgtgtg tttcgaattt tttttgaac gtgtctcgga ttgttgtggt gcgaattggt     1206
tgtttctgtc gctatggtga gatagtgtca cgtttctttc tctaaaaaaa aaaaaaaaaa    1266
aaaaaaaaaa aaaaaaa                                                   1283

<210> SEQ ID NO 12
<211> LENGTH: 305
<212> TYPE: PRT
<213> ORGANISM: Zea mays

<400> SEQUENCE: 12

Met Glu Phe Trp Gly Leu Glu Val Lys Pro Gly Ser Thr Val Lys Cys
  1               5                  10                  15

Glu Pro Gly Tyr Gly Phe Val Leu His Leu Ser Gln Ala Ala Leu Gly
             20                  25                  30

Glu Ser Lys Lys Ser Asp Asn Ala Leu Met Tyr Val Lys Ile Asp Asp
         35                  40                  45
```

```
Gln Lys Leu Ala Ile Gly Thr Leu Ser Val Asp Lys Asn Pro His Ile
         50                  55                  60

Gln Phe Asp Leu Ile Phe Asp Lys Glu Phe Glu Leu Ser His Thr Ser
 65                  70                  75                  80

Lys Thr Thr Ser Val Phe Phe Thr Gly Tyr Lys Val Glu Gln Pro Phe
                 85                  90                  95

Glu Glu Asp Glu Met Asp Leu Asp Ser Glu Asp Glu Asp Glu Glu Leu
            100                 105                 110

Asn Val Pro Val Lys Glu Asn Gly Lys Ala Asp Glu Lys Lys Gln
        115                 120                 125

Lys Ser Gln Glu Lys Ala Val Ala Ala Pro Ser Lys Ser Ser Pro Asp
130                 135                 140

Ser Lys Lys Ser Lys Asp Asp Asp Ser Asp Glu Asp Glu Thr Asp
145                 150                 155                 160

Asp Ser Asp Glu Asp Glu Thr Asp Ser Asp Glu Gly Leu Ser Pro
                165                 170                 175

Glu Glu Gly Asp Asp Asp Ser Ser Asp Glu Asp Asp Thr Ser Asp Asp
            180                 185                 190

Glu Glu Glu Asp Thr Pro Thr Pro Lys Lys Pro Glu Val Gly Lys Lys
            195                 200                 205

Arg Ala Ala Glu Ser Ser Val Leu Lys Thr Pro Leu Ser Asp Lys Lys
210                 215                 220

Ala Lys Val Ala Thr Pro Ser Ser Gln Lys Thr Gly Lys Lys Gly
225                 230                 235                 240

Ala Ala Val His Val Ala Thr Pro His Pro Ala Lys Gly Lys Thr Ile
                245                 250                 255

Val Asn Asn Asp Lys Ser Val Lys Ser Pro Lys Ser Ala Pro Lys Ser
            260                 265                 270

Gly Val Pro Cys Lys Ser Cys Ser Lys Ser Phe Ile Ser Glu Thr Ala
        275                 280                 285

Leu Gln Ala His Ser Lys Ala Asn Met Gly Ala Ser Glu Ser Gln Val
    290                 295                 300

Gln
305

<210> SEQ ID NO 13
<211> LENGTH: 1191
<212> TYPE: DNA
<213> ORGANISM: Zea mays
<220> FEATURE:
<221> NAME/KEY: CDS
<222> LOCATION: (63)..(971)

<400> SEQUENCE: 13
tccacccggc ggcttaaacc ctagttctca ctcccatcgc cgcttcagct ccgccgctgc      60 ag atg gag ttc tgg ggt ctc gag gtc aag cct ggt tcc act gtt aag       107
   Met Glu Phe Trp Gly Leu Glu Val Lys Pro Gly Ser Thr Val Lys
    1               5                  10                  15 tgt gag cct gga tat ggc ttt gtg ctg cac ctt tcc cag gct gct ctt      155
Cys Glu Pro Gly Tyr Gly Phe Val Leu His Leu Ser Gln Ala Ala Leu
                 20                  25                  30 ggg gaa tcg aag aag agt gat aat gcc ttg atg tat gtc aaa att gat      203
Gly Glu Ser Lys Lys Ser Asp Asn Ala Leu Met Tyr Val Lys Ile Asp
             35                  40                  45 gat cag aaa ctt gcc att gga acc ctc tct gtt gac aag aac cca cac      251
Asp Gln Lys Leu Ala Ile Gly Thr Leu Ser Val Asp Lys Asn Pro His
```

```
att caa ttt gat ctg att ttc gat aaa gag ttt gag ctg tcg cac aca    299
Ile Gln Phe Asp Leu Ile Phe Asp Lys Glu Phe Glu Leu Ser His Thr
        65                  70                  75 tca aaa act acc agc gtc ttc ttc act ggc tac aag gtt gaa cag cca    347
Ser Lys Thr Thr Ser Val Phe Phe Thr Gly Tyr Lys Val Glu Gln Pro
 80                  85                  90                  95 ttc gag gaa gat gaa atg gat ctt gat tct gaa gat gaa gac gag gag    395
Phe Glu Glu Asp Glu Met Asp Leu Asp Ser Glu Asp Glu Asp Glu Glu
                    100                 105                 110 ctg aat gtt cca gta gtc aag gaa aat ggc aaa gct gat ggg aag aaa    443
Leu Asn Val Pro Val Val Lys Glu Asn Gly Lys Ala Asp Gly Lys Lys
                115                 120                 125 cag aaa agt caa gaa aag gca gtt gct gca cct tca aaa tca agt ccg    491
Gln Lys Ser Gln Glu Lys Ala Val Ala Ala Pro Ser Lys Ser Ser Pro
        130                 135                 140 gat tcc aag aag agc aag gat gac gat gat tct gat gag gac gag act    539
Asp Ser Lys Lys Ser Lys Asp Asp Asp Asp Ser Asp Glu Asp Glu Thr
145                 150                 155 gat gat tct gat gag gat gag acg gac gat tct gat gag ggt tta tct    587
Asp Asp Ser Asp Glu Asp Glu Thr Asp Asp Ser Asp Glu Gly Leu Ser
160                 165                 170                 175 tct gaa gaa ggc gat gat gat tca agt gat gaa gat gat acc agt gac    635
Ser Glu Glu Gly Asp Asp Asp Ser Ser Asp Glu Asp Asp Thr Ser Asp
                180                 185                 190 gat gag gag gaa gac act cca act cct aag aag cct gag gta ggc aag    683
Asp Glu Glu Glu Asp Thr Pro Thr Pro Lys Lys Pro Glu Val Gly Lys
                195                 200                 205 aag aga gct gct gaa agt tcc gtg ctg aaa act cct cta tct gat aag    731
Lys Arg Ala Ala Glu Ser Ser Val Leu Lys Thr Pro Leu Ser Asp Lys
        210                 215                 220 aaa gca aag gtt gcc aca ccg tca tct cag aag aca ggt ggc aag aag    779
Lys Ala Lys Val Ala Thr Pro Ser Ser Gln Lys Thr Gly Gly Lys Lys
        225                 230                 235 ggc gcc gcg gtc cat gtg gca act cca cac cca gca aaa ggc aag acc    827
Gly Ala Ala Val His Val Ala Thr Pro His Pro Ala Lys Gly Lys Thr
240                 245                 250                 255 att gta aac aat gac aaa tcg gtc aag tct cca aaa tct gcg cca aaa    875
Ile Val Asn Asn Asp Lys Ser Val Lys Ser Pro Lys Ser Ala Pro Lys
                260                 265                 270 tct ggt ggc tcg gtc cct tgc aaa tcg tgc agc aag tca ttc atc agt    923
Ser Gly Gly Ser Val Pro Cys Lys Ser Cys Ser Lys Ser Phe Ile Ser
        275                 280                 285 gag acg gca ctt cag gct cac tcg aag gcg aag cat ggg ggc aag tga    971
Glu Thr Ala Leu Gln Ala His Ser Lys Ala Lys His Gly Gly Lys
        290                 295                 300 gtcgcaggtc caatagagtc cgcaacaaat gcgaaacatg ggagaggagg gtaagcgaga    1031
gtctcgaaag agtgtcggtg gaagtaggcc taaccttatt ttgtttagag acgggctatg    1091
cgttcgatgt agcaaaacaa ggctgtggtt tgtgtacttc aatatttggg ttgtgtgttt    1151 cgatttttt ttaaaaaaaa aaaaaaaaaa aaaaaaaaa                            1191
```

<210> SEQ ID NO 14
<211> LENGTH: 302
<212> TYPE: PRT
<213> ORGANISM: Zea mays

<400> SEQUENCE: 14

Met Glu Phe Trp Gly Leu Glu Val Lys Pro Gly Ser Thr Val Lys Cys

```
              1               5              10              15
         Glu Pro Gly Tyr Gly Phe Val Leu His Leu Ser Gln Ala Ala Leu Gly
                        20                  25                  30
         Glu Ser Lys Lys Ser Asp Asn Ala Leu Met Tyr Val Lys Ile Asp Asp
                35                  40                  45
         Gln Lys Leu Ala Ile Gly Thr Leu Ser Val Asp Lys Asn Pro His Ile
             50                  55                  60
         Gln Phe Asp Leu Ile Phe Asp Lys Glu Phe Glu Leu Ser His Thr Ser
         65                  70                  75                  80
         Lys Thr Thr Ser Val Phe Phe Thr Gly Tyr Lys Val Glu Gln Pro Phe
                         85                  90                  95
         Glu Glu Asp Glu Met Asp Leu Asp Ser Glu Asp Glu Asp Glu Glu Leu
                    100                 105                 110
         Asn Val Pro Val Val Lys Glu Asn Gly Lys Ala Asp Gly Lys Lys Gln
                    115                 120                 125
         Lys Ser Gln Glu Lys Ala Val Ala Ala Pro Ser Lys Ser Ser Pro Asp
             130                 135                 140
         Ser Lys Lys Ser Lys Asp Asp Asp Ser Asp Glu Asp Glu Thr Asp
         145                 150                 155                 160
         Asp Ser Asp Glu Asp Glu Thr Asp Asp Ser Asp Glu Gly Leu Ser Ser
                         165                 170                 175
         Glu Glu Gly Asp Asp Asp Ser Ser Asp Glu Asp Asp Thr Ser Asp Asp
                    180                 185                 190
         Glu Glu Glu Asp Thr Pro Thr Pro Lys Lys Pro Glu Val Gly Lys Lys
                    195                 200                 205
         Arg Ala Ala Glu Ser Ser Val Leu Lys Thr Pro Leu Ser Asp Lys Lys
             210                 215                 220
         Ala Lys Val Ala Thr Pro Ser Ser Gln Lys Thr Gly Gly Lys Lys Gly
         225                 230                 235                 240
         Ala Ala Val His Val Ala Thr Pro His Pro Ala Lys Gly Lys Thr Ile
                         245                 250                 255
         Val Asn Asn Asp Lys Ser Val Lys Ser Pro Lys Ser Ala Pro Lys Ser
                    260                 265                 270
         Gly Gly Ser Val Pro Cys Lys Ser Cys Ser Lys Ser Phe Ile Ser Glu
             275                 280                 285
         Thr Ala Leu Gln Ala His Ser Lys Ala Lys His Gly Gly Lys
             290                 295                 300

<210> SEQ ID NO 15
<211> LENGTH: 1245
<212> TYPE: DNA
<213> ORGANISM: Zea mays
<220> FEATURE:
<221> NAME/KEY: CDS
<222> LOCATION: (84)..(1019)

<400> SEQUENCE: 15
ggcacgaggt ccggtctttc cgttacccgg cggctttaaa ccctagttcc cattccatct              60
tcgtttccgc tccgccgccg tcg atg gag ttc tgg ggt ctc gag gtc aaa cct            113
                          Met Glu Phe Trp Gly Leu Glu Val Lys Pro
                            1               5                  10 gga tcc act gtc aag tgt gag cct gga cat ggc ttt atc ctg cac gtt              161
Gly Ser Thr Val Lys Cys Glu Pro Gly His Gly Phe Ile Leu His Val
                15                  20                  25 tcc cag gct gcc ctt ggg gaa tca aag aaa agt gac agt gcc tta atg              209
Ser Gln Ala Ala Leu Gly Glu Ser Lys Lys Ser Asp Ser Ala Leu Met
```

```
                30                    35                    40
tat gtc aaa gtt gat gac aag aag ctt gcc att gga acg ctc tct atc    257
Tyr Val Lys Val Asp Asp Lys Lys Leu Ala Ile Gly Thr Leu Ser Ile
         45                   50                   55 gac aaa tac cca cag ata caa ttc gat ttg gtt ttc aat aaa gag ttt    305
Asp Lys Tyr Pro Gln Ile Gln Phe Asp Leu Val Phe Asn Lys Glu Phe
 60                   65                   70 gag ctg tca cac aca tcg aaa act acc agt gta ttt ttc tct ggt tac    353
Glu Leu Ser His Thr Ser Lys Thr Thr Ser Val Phe Phe Ser Gly Tyr
 75                   80                   85                   90 aag gtt gag cag cca att gag gga gat gaa atg gat ctt gat tct gag    401
Lys Val Glu Gln Pro Ile Glu Gly Asp Glu Met Asp Leu Asp Ser Glu
         95                  100                  105 gat gaa gag gag gag cta aac att cca gta atc aag gaa aat ggc aaa    449
Asp Glu Glu Glu Glu Leu Asn Ile Pro Val Ile Lys Glu Asn Gly Lys
            110                  115                  120 gct gat ggg aag gag gag cag aaa aat caa gag aag gca gta gct gct    497
Ala Asp Gly Lys Glu Glu Gln Lys Asn Gln Glu Lys Ala Val Ala Ala
        125                  130                  135 aca gct tca aaa tca agt ctt ggc ctt gaa aag aaa agc aag gat gac    545
Thr Ala Ser Lys Ser Ser Leu Gly Leu Glu Lys Lys Ser Lys Asp Asp
    140                  145                  150 tct gat gat tct gat gag gat gag tct gat gat tct gat gag gat gat    593
Ser Asp Asp Ser Asp Glu Asp Glu Ser Asp Asp Ser Asp Glu Asp Asp
155                  160                  165                  170 tct gat gat tct gat gaa ggc gag gga tta tct cct gac gaa ggc gat    641
Ser Asp Asp Ser Asp Glu Gly Glu Gly Leu Ser Pro Asp Glu Gly Asp
                175                  180                  185 gat gat tca agt gat gag gat gat acc agt gat gat gac gag gaa gaa    689
Asp Asp Ser Ser Asp Glu Asp Asp Thr Ser Asp Asp Asp Glu Glu Glu
            190                  195                  200 acc cca act cct aaa aag cca gag gca ggc aag aag aga ggt gct gaa    737
Thr Pro Thr Pro Lys Lys Pro Glu Ala Gly Lys Lys Arg Gly Ala Glu
        205                  210                  215 aat gct ctg aaa acg cct ctt tct gat aag aaa gca aag gtt gcc aca    785
Asn Ala Leu Lys Thr Pro Leu Ser Asp Lys Lys Ala Lys Val Ala Thr
    220                  225                  230 ccg cca gcc cag aaa aca ggt ggc aag aag ggt gcc acc cat gtg gca    833
Pro Pro Ala Gln Lys Thr Gly Gly Lys Lys Gly Ala Thr His Val Ala
235                  240                  245                  250 act cca cac cca gca aaa ggc aag acc cct gca aac aat gac aaa tca    881
Thr Pro His Pro Ala Lys Gly Lys Thr Pro Ala Asn Asn Asp Lys Ser
                255                  260                  265 acg gag aag tct cca aaa tct ggt ggg tca gtc cct tgc aaa tca tgc    929
Thr Glu Lys Ser Pro Lys Ser Gly Gly Ser Val Pro Cys Lys Ser Cys
            270                  275                  280 agc aag aca ttc aat agt gag atg gct ctg cag gct cac tcc aag gcg    977
Ser Lys Thr Phe Asn Ser Glu Met Ala Leu Gln Ala His Ser Lys Ala
        285                  290                  295 aac atg ggg cca aat gag ttg cag gtc caa ctg agt cca tga            1019
Asn Met Gly Pro Asn Glu Leu Gln Val Gln Leu Ser Pro
    300                  305                  310 aggagaagca tggtggccaa gtgagtcgaa gtccattcga gtccatgaag gtgaagcatg    1079
ggagatccaa gcgagtctgg aaagattgtc gatgttagta ggctgtcctt attttgttta    1139
gagacttgtg gctatgtgat tgatgtagcg aaacaaggct gtgatgtgtt aactctgcct    1199
tataatattt tggttgaacg tgctaaaaaa aaaaaaaaaa aaaaaa                    1245
```

```
<210> SEQ ID NO 16
<211> LENGTH: 311
<212> TYPE: PRT
<213> ORGANISM: Zea mays

<400> SEQUENCE: 16

Met Glu Phe Trp Gly Leu Glu Val Lys Pro Gly Ser Thr Val Lys Cys
 1               5                  10                  15

Glu Pro Gly His Gly Phe Ile Leu His Val Ser Gln Ala Ala Leu Gly
             20                  25                  30

Glu Ser Lys Lys Ser Asp Ser Ala Leu Met Tyr Val Lys Val Asp Asp
         35                  40                  45

Lys Lys Leu Ala Ile Gly Thr Leu Ser Ile Asp Lys Tyr Pro Gln Ile
     50                  55                  60

Gln Phe Asp Leu Val Phe Asn Lys Glu Phe Glu Leu Ser His Thr Ser
 65                  70                  75                  80

Lys Thr Thr Ser Val Phe Phe Ser Gly Tyr Lys Val Glu Gln Pro Ile
                 85                  90                  95

Glu Gly Asp Glu Met Asp Leu Asp Ser Glu Asp Glu Glu Glu Glu Leu
            100                 105                 110

Asn Ile Pro Val Ile Lys Glu Asn Gly Lys Ala Asp Gly Lys Glu Glu
        115                 120                 125

Gln Lys Asn Gln Glu Lys Ala Val Ala Ala Thr Ala Ser Lys Ser Ser
    130                 135                 140

Leu Gly Leu Glu Lys Lys Ser Lys Asp Asp Ser Asp Ser Asp Ser Asp Glu
145                 150                 155                 160

Asp Glu Ser Asp Asp Ser Asp Glu Asp Ser Asp Asp Ser Asp Glu
                165                 170                 175

Gly Glu Gly Leu Ser Pro Asp Glu Gly Asp Asp Ser Ser Asp Glu
            180                 185                 190

Asp Asp Thr Ser Asp Asp Glu Glu Thr Pro Thr Pro Lys Lys
    195                 200                 205

Pro Glu Ala Gly Lys Lys Arg Gly Ala Glu Asn Ala Leu Lys Thr Pro
210                 215                 220

Leu Ser Asp Lys Lys Ala Lys Val Ala Thr Pro Pro Ala Gln Lys Thr
225                 230                 235                 240

Gly Gly Lys Lys Gly Ala Thr His Val Ala Thr Pro His Pro Ala Lys
                245                 250                 255

Gly Lys Thr Pro Ala Asn Asn Asp Lys Ser Thr Glu Lys Ser Pro Lys
            260                 265                 270

Ser Gly Gly Ser Val Pro Cys Lys Ser Cys Ser Lys Thr Phe Asn Ser
        275                 280                 285

Glu Met Ala Leu Gln Ala His Ser Lys Ala Asn Met Gly Pro Asn Glu
    290                 295                 300

Leu Gln Val Gln Leu Ser Pro
305                 310

<210> SEQ ID NO 17
<211> LENGTH: 1307
<212> TYPE: DNA
<213> ORGANISM: Zea mays
<220> FEATURE:
<221> NAME/KEY: CDS
<222> LOCATION: (87)..(944)

<400> SEQUENCE: 17
gctaaaccct aaacccagca ccagcgcccc caatcctcca acttccactc gagtagggtt      60
```

```
ctgccggccg tttcctcgtc gtcgca atg gag ttc tgg ggt gaa gaa gtg aag      113
                             Met Glu Phe Trp Gly Glu Glu Val Lys
                              1               5 cca gga gcc acg gtt tct tgc aaa gtt ggt gat ggt ttg gtt atc cac       161
Pro Gly Ala Thr Val Ser Cys Lys Val Gly Asp Gly Leu Val Ile His
 10              15                  20                  25 ctt tca cag gct gcc cta ggg gaa cca aag aaa gcg agt gag aat gcc       209
Leu Ser Gln Ala Ala Leu Gly Glu Pro Lys Lys Ala Ser Glu Asn Ala
                 30                  35                  40 att gtg tct gtc aaa att gat gat aag aaa cta gtg ctt gga acc tta       257
Ile Val Ser Val Lys Ile Asp Asp Lys Lys Leu Val Leu Gly Thr Leu
                     45                  50                  55 tca gtt gag aag cat cct caa atc tct tgt gat ctg gta ttt gat aaa       305
Ser Val Glu Lys His Pro Gln Ile Ser Cys Asp Leu Val Phe Asp Lys
             60                  65                  70 gat ttt gag tta tca cac aat tca aag aca gct agt gtt ttc ttc tgt       353
Asp Phe Glu Leu Ser His Asn Ser Lys Thr Ala Ser Val Phe Phe Cys
     75                  80                  85 ggc tac aag tca cct gtt cct ctg ttt gag tct gat tct ggt gaa gat       401
Gly Tyr Lys Ser Pro Val Pro Leu Phe Glu Ser Asp Ser Gly Glu Asp
 90              95                  100                 105 agt tca gat gaa gag gtt gaa ccc gat cta att cca atg cag aat aat       449
Ser Ser Asp Glu Glu Val Glu Pro Asp Leu Ile Pro Met Gln Asn Asn
                 110                 115                 120 gaa att aaa att tct act gca aag gtt ccc gtg aag gtt ggt ata caa       497
Glu Ile Lys Ile Ser Thr Ala Lys Val Pro Val Lys Val Gly Ile Gln
                     125                 130                 135 aat gct gat gaa gat gaa act tct agt ggt gat gat gat gat ttc act       545
Asn Ala Asp Glu Asp Glu Thr Ser Ser Gly Asp Asp Asp Asp Phe Thr
             140                 145                 150 gat agt gat agt gaa atg tct gag gaa gat gag tcc agt gat gaa gat       593
Asp Ser Asp Ser Glu Met Ser Glu Glu Asp Glu Ser Ser Asp Glu Asp
     155                 160                 165 gaa gtg tca agc gat aca gat act agt gat gat tct ggt tcg gaa gaa      641
Glu Val Ser Ser Asp Thr Asp Thr Ser Asp Asp Ser Gly Ser Glu Glu
170                 175                 180                 185 cag aca cct acc cca aag aag act gag gta gta gtt ggc aag aag agg       689
Gln Thr Pro Thr Pro Lys Lys Thr Glu Val Val Val Gly Lys Lys Arg
                 190                 195                 200 gca att gaa gct gag aca cct tct ggt aag aag gct aag tct gaa caa       737
Ala Ile Glu Ala Glu Thr Pro Ser Gly Lys Lys Ala Lys Ser Glu Gln
                     205                 210                 215 tct gct cag aaa aca ggc gac aag gtc tca act tct cat cct gca aag       785
Ser Ala Gln Lys Thr Gly Asp Lys Val Ser Thr Ser His Pro Ala Lys
             220                 225                 230 cag tcc agc aag act cct gca gac aaa tct aca aag acc ccc aca gct       833
Gln Ser Ser Lys Thr Pro Ala Asp Lys Ser Thr Lys Thr Pro Thr Ala
     235                 240                 245 gac aag aag tcc ccc aaa tct ggg agc cat gcc tgc aag tca tgc agc       881
Asp Lys Lys Ser Pro Lys Ser Gly Ser His Ala Cys Lys Ser Cys Ser
250                 255                 260                 265 aaa tct ttc ggc agt gcg tca gca ctt gag tct cat cag aag gca aag       929
Lys Ser Phe Gly Ser Ala Ser Ala Leu Glu Ser His Gln Lys Ala Lys
                 270                 275                 280 aag cat gaa gcc tag agcacgtgct ataccatcta ctcgttatca aaatcagtgg       984
Lys His Glu Ala
             285 tcttattttt gaacttgaaa atgtccaagt ttggaacttg cccagtagtc atctgattag    1044
```

-continued

```
tggtgttatt tttctttgaa cttgggaatt gtctagtttg ggacatacgc ggtatgcctg    1104
gttaagaaca tgggaaatgt caggttagaa caggtcctgc tggcccagtt ttggtcgtcg    1164
tcgaatgttg ctaatgttgg aactgattat tgtgacccgt aaggccgtaa gggagaatct    1224
ttgttatctg gtagtgccta gtgcaaatca ccttttctc agttgttaaa catcttgctt    1284
ttaaaaaaaa aaaaaaaaaa aaa                                            1307
```

<210> SEQ ID NO 18
<211> LENGTH: 285
<212> TYPE: PRT
<213> ORGANISM: Zea mays

<400> SEQUENCE: 18

```
Met Glu Phe Trp Gly Glu Val Lys Pro Gly Ala Thr Val Ser Cys
 1               5                  10                  15

Lys Val Gly Asp Gly Leu Val Ile His Leu Ser Gln Ala Ala Leu Gly
            20                  25                  30

Glu Pro Lys Lys Ala Ser Glu Asn Ala Ile Val Ser Val Lys Ile Asp
        35                  40                  45

Asp Lys Lys Leu Val Leu Gly Thr Leu Ser Val Glu Lys His Pro Gln
    50                  55                  60

Ile Ser Cys Asp Leu Val Phe Asp Lys Asp Phe Glu Leu Ser His Asn
65                  70                  75                  80

Ser Lys Thr Ala Ser Val Phe Phe Cys Gly Tyr Lys Ser Pro Val Pro
                85                  90                  95

Leu Phe Glu Ser Asp Ser Gly Glu Asp Ser Ser Asp Glu Glu Val Glu
            100                 105                 110

Pro Asp Leu Ile Pro Met Gln Asn Asn Glu Ile Lys Ile Ser Thr Ala
        115                 120                 125

Lys Val Pro Val Lys Val Gly Ile Gln Asn Ala Asp Glu Asp Glu Thr
    130                 135                 140

Ser Ser Gly Asp Asp Asp Asp Phe Thr Asp Ser Asp Ser Glu Met Ser
145                 150                 155                 160

Glu Glu Asp Glu Ser Ser Asp Glu Asp Glu Val Ser Ser Asp Thr Asp
                165                 170                 175

Thr Ser Asp Asp Ser Gly Ser Glu Glu Gln Thr Pro Thr Pro Lys Lys
            180                 185                 190

Thr Glu Val Val Val Gly Lys Lys Arg Ala Ile Glu Ala Glu Thr Pro
        195                 200                 205

Ser Gly Lys Lys Ala Lys Ser Glu Gln Ser Ala Gln Lys Thr Gly Asp
    210                 215                 220

Lys Val Ser Thr Ser His Pro Ala Lys Gln Ser Ser Lys Thr Pro Ala
225                 230                 235                 240

Asp Lys Ser Thr Lys Thr Pro Thr Ala Asp Lys Lys Ser Pro Lys Ser
                245                 250                 255

Gly Ser His Ala Cys Lys Ser Cys Ser Lys Ser Phe Gly Ser Ala Ser
            260                 265                 270

Ala Leu Glu Ser His Gln Lys Ala Lys Lys His Glu Ala
        275                 280                 285
```

MAIZE HISTONE DEACETYLASES AND THEIR USE

CROSS-REFERENCE TO RELATED APPLICATION

This application is a divisional of U.S. application Ser. No. 09/282,305 filed Mar. 31, 1999, now issued as U.S. Pat. No. 6,287,843, and Provisional Application No. 60/080,563, filed Apr. 3, 1998, which is hereby incorporated herein in its entirety by reference.

FIELD OF THE INVENTION

The invention relates to the field of the genetic manipulation of plants, particularly the modulation of gene activity in plants and increased disease resistance.

BACKGROUND OF THE INVENTION

Histones are the protein portion of a protein-DNA complex termed the nucleosome. The acetylation of the $\Sigma$-amino group of specific lysines present in the amino termini of histones has been correlated with both increased and decreased gene activity.

Nucleosomes structurally organize chromosomal DNA to form chromatin. The degree of interaction between histones and DNA varies between regions undergoing transcription and regions not being transcribed. The histones in chromatin regions containing active promoters are often post-translationally modified with acetyl groups covalently attached to specific lysine residues.

Hyperacetylated histones are thought to adopt a chromatin structure that allows other proteins to bind promoter DNA and activate transcription. Inactive promoters are associated with hypoacetylated histones, and removal of the acetyl groups from histones in normally active chromatin will repress transcription in that region.

Histone deacetylase (HD), responsible for removing acetyl modifications, may be localized to promoters targeted for repression by other proteins that associate with HD and specifically bind regulatory elements in promoter DNA.

Crop losses from pathogen infections are substantial and consume considerable quantities of productive plant biomass. It is generally believed that plant pathogens must find a way to suppress elicitation, the mechanism by which an elicitor, a pathogen-derived compound, induces disease gene expression upon recognition by the host.

One necrotrophic pathogen, the filamentous fungus *Cochliobolus carbonum* race 1, synthesizes a cyclic tetrapeptide, HC-toxin. HC-toxin is absolutely required for pathogenicity and is a specific inhibitor of HD activity. Resistant maize genotypes produce an HC-toxin reductase encoded by the nuclear Hm locus, which abolishes toxin activity by reducing the ketone group. These plants develop small expanding lesions in response to inoculation with Tox2$^+$ isolates of *C. carbonum*, similar to the lesions formed by Tox2$^-$ isolates regardless of the host genotype. HC-toxin acts in a cytostatic manner. It is not toxic to plant cells and does not determine pathogenicity by simply killing host cells prior to colonization.

Acetylation thus plays a key role in gene activation and in some instances invasion by pathogens. Mechanisms are therefore needed to control acetylation that may control gene activity and potentially play a role in disease resistance.

SUMMARY OF THE INVENTION

Compositions and methods for modulating gene activity states are provided. The compositions comprise histone deacetylases and nucleotide sequences encoding these enzymes, as well as nucleotide sequences encoding the corresponding antisense sequences to the histone deacetylases. The nucleotide sequences can be used to transform plants and alter the histone acetylation, heterochromatin, chromatin assembly, and gene activity of the transformed plants. In this manner, transformed plants having altered gene activity and enhanced disease resistance can be obtained.

Additionally, compositions of the invention find use in screening for toxins that affect pathogenicity and in determining which disease response promoters are regulated by histone deacetylase.

DETAILED DESCRIPTION OF THE INVENTION

Figure 1:
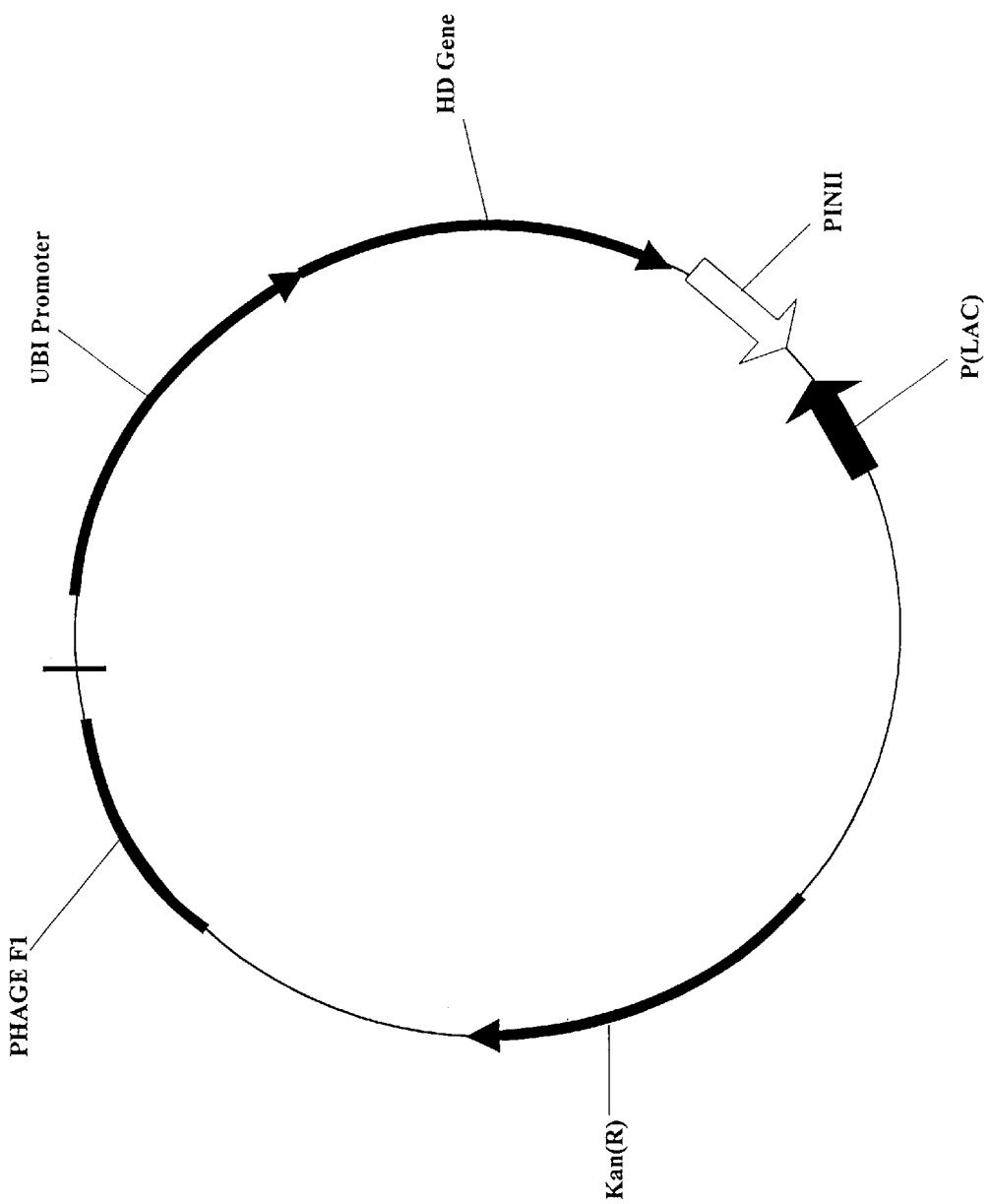
FIG. 1 provides a vector for expression of the histone deacetylase genes of the invention.

Maize histone deacetylase enzymes and nucleotide sequences encoding the enzymes are provided. The nucleotide sequences or corresponding antisense sequences can be utilized to transform plants and change the plant nucleosomal conformation, modulating or regulating gene activity.

Nucleotide sequences encoding nine maize histone deacetylase enzymes are provided. See SEQ ID NOs: 1, 3, 5, 7, 9, 11, 13, 15, and 17. The sequences of five of the HD cDNAs (family 1, ZmHD 1) appear to be regulators of promoters for RNA polymerase II, the enzyme responsible for transcription of genes encoding enzymes and other proteins. The sequences of the remaining four (family 2, ZmHD2) appear to affect chromatin structure at promoters for RNA polymerase I and thus regulate ribosomal RNA (rRNA) production.

In particular, the present invention provides for isolated nucleic acid molecules comprising nucleotide sequences encoding the amino acid sequences shown in SEQ ID NOs: 2, 4, 6, 8, 10, 12, 14, 16, and 18, or the nucleotide sequences deposited in a bacterial host as ATCC Accession Nos. 98720, 98719, 98717, 98718, 207183, 98716, 98723, 98722, and 98721. Further provided are polypeptides having an amino acid sequence encoded by a nucleic acid molecule described herein, for example those set forth in SEQ ID NOs: 1, 3, 5, 7, 9, 11, 13, 15, and 17, those deposited as ATCC Accession Nos. 98720, 98719, 98717, 98718, 207183, 98716, 98723, 98722, and 98721, and fragments and variants thereof.

Plasmids containing the nucleotide sequences of the invention were deposited with American Type Culture Collection (ATCC), Manassas, Va., on Apr. 2, 1998, and assigned Accession Nos. 98720, 98719, 98717, 98718, 98716, 98723, 98722, and 98721, and on Mar. 31, 1999, and assigned Accession No. 207183. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112.

Thus, the invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably, culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence modulate or regulate gene activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the entire nucleotide sequence encoding the proteins of the invention.

A fragment of an HD nucleotide sequence that encodes a biologically active portion of an HD protein of the invention will encode at least 15, 25, 30, 50, 100, 150, 200, 250, 300, 350, 400, or 450 contiguous amino acids, or up to the total number of amino acids present in a full-length HD protein of the invention (for example, 458, 351, 439, 517, 432, 305, 302, 311, or 285 amino acids for SEQ ID NO: 2, 4, 6, 8, 10, 12, 14, 16, or 18, respectively). Fragments of an HD nucleotide sequence that are useful as hybridization probes for PCR primers generally need not encode a biologically active portion of an HD protein.

A fragment of an HD nucleotide sequence may encode a biologically active portion of an HD protein, or it may be a fragment that can be used as a hybridization probe or PCR primer using methods disclosed below. A biologically active portion of an HD protein can be prepared by isolating a portion of one of the HD nucleotide sequences of the invention, expressing the encoded portion of the HD protein (e.g., by recombinant expression in vitro), and assessing the activity of the encoded portion of the HD protein. Nucleic acid molecules that are fragments of an HD nucleotide sequence comprise at least 15, 20, 50, 75, 100, 325, 350, 375, 400, 425, 450, 500, 550, 600, 650, 700, 800, 900, 1,000, 1,100, 1,200, 1,300, or 1,400 nucleotides, or up to the number of nucleotides present in a full-length HD nucleotide sequence disclosed herein (for example, 1826, 1475, 2019, 1943, 1576, 1283, 1191, 1245, or 1307 nucleotides for SEQ ID NO: 1, 3, 5, 7, 9, 11, 13, 15, or 17, respectively).

By "variants" is intended substantially similar sequences. For nucleotide sequences, conservative variants include those sequences that, because of the degeneracy of the genetic code, encode the amino acid sequence of an HD protein of the invention. Generally, nucleotide sequence variants of the invention will have at least 70%, generally, 80%, preferably up to 90% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. For example, amino acid sequence variants of the histone deacetylase proteins can be prepared by mutations in the DNA. Methods for mutagenesis and nucleotide sequence alterations are well known in the art. See, for example, Kunkel (1985) *Proc. Natl. Acad. Sci. USA* 82: 488–492; Kunkel et aL (1987) *Methods in Enzymol.* 154: 367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas ofProtein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the histone deacetylases as well as components and fragments thereof. That is, it is recognized that component polypeptides or fragments of the proteins may be produced which retain activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by the in vitro assays measuring acetylation or by its effect on the plant defense system. See, for example U.S. Pat. No. 5,614, 395, herein incorporated by reference.

It is recognized that with these nucleotide sequences, antisense constructions, complementary to at least a portion of the messenger RNA (mRNA) for the histone deacetylases can be constructed. Antisense nucleotides are constructed to hybridize with the corresponding mRNA. Therefore, modifications of the sequences may be made as long as the sequences hybridize to and interfere with expression of the corresponding mRNA. In this manner, antisense constructions having 70%, preferably 80%, more preferably 85% sequence similarity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the invention can be used to isolate other corresponding or homologous sequences, including those in other plant species. In this manner, methods such as PCR, hybridization, and the like can be used to identify such sequences based on their sequence homology to the sequences set forth herein. Sequences isolated based on their sequence identity to the entire HD coding sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like. In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the HD coding sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire histone deacetylase sequence or portions thereof may be used as probes capable of specifically hybridizing to corresponding coding sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify the HD coding sequences of interest from a chosen organism by the well-know process of polymerase chain reaction (PCR). This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1X to 2X SSC. (20X SSC. =3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5X to 1X SSC at 55 to 60° C. Exemplary high stringency conditions include hybridization in 50% formamide, 1 M NaCl, 1% SDS at 37° C., and a wash in 0.1X SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138: 267–284: $T_m=81.5°$ C.$+16.6$ (log M)$+0.41$ (%GC)$-0.61$ (% form)$-500/L$; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1 ° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C.

(formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, sequences that code for the histone deacetylase and other histone deacetylase proteins of the invention and hybridize to the sequences disclosed herein will be at least 40% to 50% homologous, 60% to 70% homologous, and even 80%, 85%, 90%, 95% homologous or more with the disclosed sequence. That is, the sequence similarity of sequences may range, sharing at least about 40%, 50%, about 60%, 70%, and even about 80%, 85%, 90%, 95%, 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl. Math.* 2: 482; by the homology alignment algorithm of Needleman et al. (1970) *J. Mol Biol.* 48: 443; by the search for similarity method of Pearson et al. (1988) *Proc. Natl. Acad. Sci.* 85: 2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) *Gene* 73: 237–244 (1988); Higgins et al. (1989) *CABIOS* 5: 151–153; Corpet et al. (1988) *Nucleic Acids Res.* 16: 10881–90; Huang et al. (1992) *Computer Applications in the Biosciences* 8: 155–65, and Person et al. (1994) *Meth. Mol. Biol.* 24: 307–331; preferred computer alignment methods also include the BLASTP, BLASTN, and BLASTX algorithms (see Altschul et al (1990) *J. Mol. Biol.* 215: 403–410). Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using default parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48: 443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleotide sequences of the invention are useful for modulating gene activity. By "modulating gene activity" is intended the increase or decrease in activity states of a gene or gene regions. Since both inactive and active genes are highly enriched in an acetylated nucleosome fraction, acetylation is not merely a consequence of gene activity. Furthermore, "modulating gene activity" also encompasses a general means of preparing a gene for transcription. Thus, the nucleotide sequences of the invention act to modulate gene activity in various manners. Increased histone acetylation may enhance the ability of transcription factors to bind to DNA when contained in a nucleosome.

The nucleotide sequences contained in SEQ ID NOs: 1, 3, 5, 7, 9, 11, 13, 15, and 17, as well as corresponding antisense sequences, may be used in expression cassettes to transform target plants. Generally, the transformation and expression of such sequences in the plant cell may lead to an increase or alternatively, a decrease in gene activity. The nucleotide sequences of the invention may be tested for their specific effect on gene activity. Such assays are available in the art, as discussed below.

It is further recognized that the constructs of the invention may globally modulate gene activity or alternatively, may target particular regions of the chromosome. Assays are available for determining activity. See, generally, Lusser et al. (1997) *Science* 277: 88–91; Rundlett et al. (1996) *PNAS* 93: 14503–14508; DeRubertis et al. (1996) *Nature* 384: 589–591; Pazin et al. (1997) *Cell* 89: 325–328; herein incorporated by reference. See also, Walton et al. (1993) *Ann. Rev. Phytopathol.* 31: 275–303; Brosch et al. (1995) *Plant Cell* 7: 1941–1950; Walton et al. (1985) *Experientia* 41: 348–350; Yoshida et al. (1995) *Bioessays* 17: 423; Taunton et al. (1996) *Science* 272: 408–411; Pazin et al. (1997) *Cell* 89: 325–328; Verreault et al. (1996) *Cell* 87: 95–104; Kaufman et al. (1997) *Genes Dev.* 11: 345–357; Parthun et al. (1996) *Cell* 87: 85–94; Ciuffetti et al. (1995) *Physiol. Mol. Pl. PathoL.* 46: 61–70; Rasmussen et al. (1988) *Physiol. Mol. Pl. Pathol.* 32: 283–292; Ciuffetti et al. (1983). *Biochem.* 22: 3507–3510; Wolf et al. (1990) *Plant Sci.* 70: 127–137; Ach et al. (1997). *Plant Cell* 9: 1595–1606. Additionally, function of the HD sequences can be elucidated by the characterization of mutants isolated by TUSC (Benson et al. (1995) *Plant Cell* 7: 75–84; Mena et al. (1996) *Science* 274: 1537–1540; U.S. Pat. No. 5,962,764) screening.

The HC-toxin of the maize pathogen *C. carbonum* and related cyclic tetrapeptides inhibit HDs and cause hyperacetylation of histones in susceptible, but not in resistant, maize strains. Perhaps, the inhibition of histone deacetylation interferes with the induction of plant defense genes mediated by RNA polymerase II transcription. Also, inhibition of deacetylation by HC-toxin may lead to a rather general inhibition of host rRNA transcription, owing to inhibition of nucleolar HD2. Thus, the sequences of the invention may be utilized to boost the plant defense mechanisms. In this manner, they can be used to transform plants to increase gene activity of the plant defense mechanism and increase the resistance of the plants to pathogen invasion.

It is recognized that the present invention is not dependent upon a particular mechanism of defense. Rather, the genes and methods of the invention work to increase resistance of the plant to pathogens independent of how that resistance is increased.

Thus, in one embodiment of the invention, the nucleotide sequences of the invention can be utilized to modulate, create, or enhance disease resistance in a plant. Accordingly, the methods are also useful in protecting plants against fungal pathogens, viruses, nematodes and the like.

By "enhanced disease resistance" is intended that the plants avoid the disease symptoms that are the outcome of plant-pathogen interactions. In the same manner, while the plant may have some effect from the pathogen, disease and plant death are avoided. That is, pathogens are prevented from causing plant diseases and the associated disease symptoms. The methods of the invention can be utilized to protect plants from disease, particularly those diseases that are caused by plant pathogens.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. glycinea, *Macrophomina phaseolina, Rhizoctonia solani, Sclerotinia sclerotiorum, Fusarium oxysporum, Diaporthe phaseolorum* var. sojae (*Phomopsis sojae*), *Diaporthe phaseolorum* var. caulivora, *Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. glycinea, *Xanthomonas campestris* p.v. phaseoli, *Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese* subsp. insidiosum, *Pythium ultimum, Pythium irregulare, Pythium splendens, Pythium debaryanum, Pythium aphanidermatum, Phytophthora megasperma, Peronospora trifoliorum, Phoma medicaginis* var. medicaginis, *Cercospora medicaginis, Pseudopeziza medicaginis, Leptotrochila medicaginis,* Fusarium, *Xanthomonas campestris* p.v. alfalfae, *Aphanomyces euteiches, Stemphylium herbarum, Stemphylium alfalfae;* Wheat: *Pseudomonas syringae* p.v. atrofaciens, *Urocystis agropyri, Xanthomonas campestris* p.v. translucens, *Pseudomonas syringae* p.v. syringae, *Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. tritici, *Puccinia graminis* f.sp. tritici, *Puccinia recondita* f.sp. tritici, *Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. tritici, *Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. carotovora, *Cephalosporium acremonium, Phytophthora cryptogea, Albugo tragopogonis;* Corn: *Fusarium moniliforme* var. subglutinans, *Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. nebraskense, *Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. zea, *Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. syringae, *Xanthomonas campestris* p.v. holcicola, *Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, lesion, and renniform nematodes, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm; *Melanotus* spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafmniner; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; Eleodes, Conoderus, and Aeolus spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; *Blissus leucopterus leucopterus,* chinch bug; *Contarinia sorghicola,* sorghum midge; *Tetranychus cinnabarinus,* carmine spider mite; *Tetranychus urticae,* twospotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia,* western cutworm; *Elasmopalpus lignosellus,* lesser cornstalk borer; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarctata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; *zygogramma exclamationis,* sunflower beetle; *Bothyrus gibbosus,* carrot beetle; *Neolasioptera murtfeldtiana,* sunflower seed midge; Cotton: *Heliothis virescens,* cotton budworm; *Helicoverpa* zea, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

The sequences of the invention, which encompass HD coding sequences and their antisense constructs, can be introduced into any plant. In this manner, the sequences to be introduced may be used in expression cassettes for expression in any plant of interest where expression in the plant is necessary for transcription.

Where expression cassettes are needed, such expression cassettes will comprise a transcriptional initiation region operably linked to the HD coding sequence or antisense sequence corresponding to the HD coding sequence of interest. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the sequence to be under the transcriptional regulation of the regulatory regions.

Thus, the transcriptional or expression cassette will include in the 5'-to-3' direction of transcription, a transcriptional and translational initiation region, a nucleotide sequence of the invention, and a transcriptional and translational termination region fuinctional in plants. The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of HD in the plant or plant cell. Thus, the phenotype of the plant or plant cell is altered.

A number of promoters are available for expression of the nucleotides of the invention in plant cells. Inducible promoters may be utilized to drive the expression of the genes, particularly pathogen-inducible promoters when enhanced disease resistance is the objective.

Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89: 245–254; Uknes et al. (1992) *Plant Cell* 4: 645–656; and Van Loon (1985) *Plant Mol. Virol.* 4: 111–116. See also WO 99/43819, published Sept. 9, 1999.

Of interest are promoters that are expressed locally at or near the site of pathogen infection. See, for example, Marineau et al. (1987) *Plant Mol. BioL* 9: 335–342; Matton et al. (1989) *Molecular Plant-Microbe Interactions* 2: 325–331; Somsisch et al. (1986) *Proc. Natl. Acad. Sci. USA* 83: 2427–2430; Somsisch et al. (1988) *Mol. Gen. Genet.* 2: 93–98; and Yang (1996) *Proc. Natl. Acad. Sci. USA* 93: 14972–14977. See also, Chen et al. (1996) *Plant J.* 10: 955–966; Zhang et al. (1994) *Proc. Natl. Acad. Sci. USA* 91: 2507–2511; Warner et al (1993) *Plant J.* 3: 191–201; Siebertz et al (1989) *Plant Cell* 1: 961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41: 189–200).

Alternatively, constitutive promoters can be utilized. Such constitutive promoters include, for example, the core promoter of the Rsyn7 (WO 99/43838 and U.S. Pat. No. 6,072,050); the core CaMV 35S promoter (Odell et al. (1985) *Nature* 313: 810–812); rice actin (McElroy et al (1990) *Plant Cell* 2: 163–171); ubiquitin (Christensen et al. (1989) *Plant Mol. Biol.* 12: 619–632 and Christensen et al. (1992) *Plant Mol. Biol* 18: 675–689); pEMU (Last et al. (1991) *Theor. Appl. Genet.* 81: 581–588); MAS (Velten et al. (1984) *EMBO J.* 3: 2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611.

Tissue-specific promoters can be utilized to target modulation of gene activity or enhanced disease resistance within a particular plant tissue. Tissue-specific promoters include Yamamoto et al. (1997) *Plant J.* 12(2)255–265; Kawamata et al. (1997) *Plant Cell Physiol.* 38(7): 792–803; Hansen et al. (1997) *Mol. Gen Genet.* 254(3): 337–343; Russell et al. (1997) *Transgenic Res.* 6(2): 157–168; Rinehart et al. (1996) *Plant Physiol* 112(3): 1331–1341; Van Camp et al. (1996)

*Plant Physiol.* 112(2): 525–535; Canevascini et al. (1996) *Plant Physiol.* 112(2): 513–524; Yamamoto et al. (1994) *Plant Cell Physiol.* 35(5): 773–778; Lam (1994) *Results Probl. Cell Differ.* 20: 181–196; Orozco et al. (1993) *Plant Mol Biol.* 23(6): 1129–1138; Matsuoka et al. (1993) *Proc Natl. Acad. Sci. USA* 90(20): 9586–9590; and Guevara-Garcia et al. (1993) *Plant J.* 4(3): 495–505. Such promoters can be modified, if necessary, for weak expression.

The termination region of the expression cassette may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262: 141–144; Proudfoot (1991) *Cell* 64: 671–674; Sanfacon et al. (1991) *Genes Dev.* 5: 141–149; Mogen et al. (1990) *Plant Cell.* 2: 1261–1272; Munroe et al. (1990) *Gene* 91: 151–158; Ballas et al. (1989) *Nucleic Acids Res.* 17: 7891–7903; Joshi et al. (1987) *Nucleic Acids Res.* 15: 9627–9639.

Where appropriate, the sequences of the invention may be optimized for increased expression in the transformed plant. That is, the sequence of interest can be synthesized using plant-preferred codons for improved expression. Methods are available in the art for synthesizing plant-preferred genes. See, for example, U.S. Pat. Nos. 5,380,831, 5,436,391, and Murray et al. (1989) *Nucleic Acids Res.* 17: 477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86: 6126–6130); potyvirus leaders, for example, TEV leader (Tobacco Etch Virus) (Allison et al. (1986); MDMV leader (Maize Dwarf Mosaic Virus); *Virology* 154: 9–20), and human immunoglobulin heavy-chain binding protein (BiP), (Macejak et al. (1991) *Nature* 353: 90–94); untranslated leader from the coat protein mRNA of alfalfa mosaic virus (AMV RNA 4) (Jobling et al. (1987) *Nature* 325: 622–625); tobacco mosaic virus leader (TMV) (Gallie et al. (1989) in *Molecular Biology of RNA,* ed. Cech (Liss, New York), pp. 237–256); and maize chlorotic mottle virus leader (MCMV) (Lommel et al. (1991) *Virology* 81: 382–385). See also, Della-Cioppa et al. (1987) *Plant Physiol.* 84: 965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The sequences of the present invention can be used to transform or transfect any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4: 320–334), electroporation (Riggs et al. (1986) *Proc. Natl. Acad. Sci. USA* 83: 5602–5606, Agrobacterium-mediated transformation (Townsend et al., U.S. Pat No. 5,563,055), direct gene transfer (Paszkowski et al. (1984) *EMBO J.* 3: 2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6: 923–926). Also see Weissinger et al. (1988) *Ann. Rev. Genet.* 22: 421–477; Sanford et al. (1987) *Particulate Science and Technology* 5: 27–37 (onion); Christou et al. (1988) *Plant Physiol.* 87: 671–674 (soybean); McCabe et al. (1988) *Bio/Technology* 6: 923–926 (soybean); Finer and McMullen (1991) *In Vitro Cell Dev. Biol.* 27P: 175–182 (soybean); Singh et al. (1998) *Theor. Appl. Genet.* 96: 319–324 (soybean); Datta et al. (1990) *Biotechnology* 8: 736–740 (rice); Klein et al. (1988) *Proc. Natl. Acad. Sci. USA* 85: 4305–4309 (maize); Klein et al. (1988) *Biotechnology* 6: 559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol* 91: 440–444 (maize); Fromm et al. (1990) *Biotechnology* 8: 833–839 (maize); Hooykaas-Van Slogteren et al. (1984) *Nature (London)* 311: 763–764; Bytebier et al. (1987) *Proc. Natl. Acad. Sci. USA* 84: 5345–5349 (Liliaceae); De Wet et al. (1985) in *The Experimental Manipulation of Ovule Tissues,* ed. Chapman et al. (Longman, N.Y.), pp. 197–209 (pollen); Kaeppler et al. (1990) *Plant Cell Reports* 9: 415–418 and Kaeppler et al. (1992) *Theor. Appl. Genet.* 84: 560–566 (whisker-mediated transformation); D'Halluin et al. (1992) *Plant Cell* 4: 1495–1505 (electroporation); Li et al. (1993) *Plant Cell Reports* 12: 250–255 and Christou and Ford (1995) *Annals of Botany* 75: 407–413 (rice); Osjoda et al. (1996) *Nature Biotechnology* 14: 745–750 (maize via *Agrobacterium tumefaciens*); all of which are herein incorporated by reference.

The modified plant may be grown into plants in accordance with conventional ways. See, for example, McCormick et al. (1986) *Plant Cell. Reports* 5: 81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The present invention also provides isolated nucleic acids comprising polynucleotides of sufficient length and complementarity to a gene of the invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of polypeptides, or for use as immunogens in the preparation and/or screening of antibodies. The isolated nucleic acids of the present invention can also be employed for use in sense or antisense suppression of one or more genes of the invention in a host cell, tissue, or plant. Attachment of chemical agents, which bind, intercalate, cleave and/or crosslink to the isolated nucleic acids of the present invention can also be used to modulate transcription or translation. Further, using a primer specific to an insertion sequence (e.g., transposon) and a primer which specifically hybridizes to an isolated nucleic acid of the present invention, one can use nucleic acid amplification to identify insertion sequence inactivated genes of the invention from a cDNA library prepared from insertion sequence mutagenized plants. Progeny seed from the plants comprising the desired inactivated gene can be grown to a plant to study the phenotypic changes characteristic of that inactivation. See, *Tools to Determine the Function of Genes,* 1995 Proceedings of the Fiftieth Annual Corn and Sorghum Industry Research Conference (American Seed Trade Association, Washington, D.C., 1995). Additionally, non-translated 5' or 3' regions of the polynucleotides of the present invention can be used to modulate turnover of heterologous mRNAs and/or protein synthesis. Further, the codon preference characteristic of the polynucleotides of the present invention can be employed in heterologous sequences, or altered in homologous or heterologous sequences, to modulate translational level and/or rates.

In another embodiment of the invention, the nucleotide sequences for HD can be utilized to produce the enzyme with greater purity. Such enzyme preparations can be utilized for assays of enzymatic activity as well as to produce anti-HD antibodies. Mechanisms for antibody production are known in the art. See, for example, Harlow and Lane (1988) *Antibodies, A Laboratory Manual* (Cold Spring Harbor Publications, New York) and the references cited therein. Such antibodies are useful to immunoprecipitate HD from cell extracts and isolate members of regulatory co-factor complexes associated with HD in vivo.

Likewise, cDNA constructs can also be tagged with short peptides for rapid detection and manipulation of the enzyme, fused to specific DNA-binding domains for directed localization to reporter gene promoters, and mutated to adjust the functional characteristics of domains within HD.

The present invention provides a method of genotyping a plant comprising a polynucleotide of the present invention. Preferably, the plant is a monocot, such as maize or sorghum. Genotyping provides a means of distinguishing homologues of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., Clark, ed. (1997) *Plant Molecular Biology: A Laboratory Manual,* Chapter 7 (Springer-Verlag, Berlin). For molecular marker methods, see generally, Paterson (1996) "The DNA Revolution," in *Genome Mapping in Plants,* ed. Paterson (Academic Press/R.G. Landis Company, Austin, Tex.), pp. 7–21.

The particular method of genotyping in the present invention may employ any number of molecular marker analytic techniques such as, but not limited to, restriction fragment length polymorphisms (RFLPs). Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement.

The present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

The following examples are offered by way of illustration and not by way of limitation.

EXPERIMENTAL

The characterization of the diverse family of HD and p48-related genes in maize has been studied. Mutational disruption of these loci has also been initiated. Nine HD genes have been isolated from maize.

Example 1

The Maize Genome Encodes At Least Nine Histone Deacetylases

Nine maize HD-encoding cDNA clones (some RPD3-like in sequence) have been identified in the PIONEER EST-databank. The large number of HD genes in maize is not surprising if considering that in the yeast S. cerevisiae, five distinct HD-related genes have been isolated and of the two HDs analyzed in detail, both are found in distinct complexes with different substrate specificities. (see, Rundlett et al. (1996) *Proc. Natl. Acad. Sci. USA* 93(25): 14503–14508). Numerous HD enzymes with different specificities (for specific Lys residues on the four core histones) must act to fine tune the acetylation state to the physiologically distinct patterns observed in vivo.

The nine HD clones can be grouped into two classes by homology to either yeast RPD3 or to a previously cloned nucleolar HD in maize, ZmHD-p39. All of the HD genes map to different chromosomal locations, and gene specific probes detect single or low copy numbers for each cDNA clone.

Mapping and initial characterization of the expression patterns of these maize HD genes has been completed. The expression patterns will be analyzed and biochemical interaction studies conducted to define which HD/MSI proteins associate. In addition, preliminary characterization of the wild type (wt) expression pattern will determine the status of any disrupted alleles. Northern blots show consistent patterns in the levels of expression among members of the ZmHD1 and ZmHD2 classes throughout the tissues and developmental stages tested. Northern blots indicate similar expression levels in roots, seedlings, ligules, mature leaves, husks, silks, immature ears, and mature cobs when probes for ZmHD1a, 1b, 2a, and 2b are used. ZmHD1c, 1d, and 2c are similarly distributed but expressed at a lower level. Expression patterns were also measured in leaves undergoing a defense response to *C. carbonum* TOX2$^-$ or exposed to the HD inhibitor HC-toxin. Neither treatment alone nor the combination altered the normal level of expression for class 1 or 2 ZmHD genes as detected in control leaves.

To characterize HD function in planta, the Trait Utility System for Corn (TUSC) will be used to isolate maize lines containing HD loci, that have been disrupted by the Mutator (Mu) transposable element. Briefly, Mu-saturated lines are crossed into inbred lines to create a collection of 40,000 F1 individuals. DNA samples isolated from these individuals are pooled and used as template DNA for PCR with a Mu element terminal inverted repeat (TIR) sequence primer in combination with HD specific primers. A DNA pool, containing a Mu element near the region encoded by the HD primer will produce a positive signal when the reaction is blotted and probed with the HD cDNA. The PCR reactions are repeated using the individual DNA samples that were part of the positive pool in order to identify F1 plants containing putative Mu-tagged HD alleles. See, Benson et al. (1995) *Plant Cell* 7: 75–84 and Mena et al. (1996) *Science* 274: 1537–1540.

Preliminary characterization of ZmMSI1 expression patterns by RNA blot hybridization show that the gene is differentially expressed in various maize tissues. ZmMSI1 mRNA is strongly upregulated in the vegetative shoot apex and detected at low levels in the roots, immature female inflorescence (ear), silks, and the developing embryo.

A. The isolation and molecular characterization of the HD and MSI gene families.

MSI-related proteins are thought to be transcription co-regulators, which bind to HDs and target them to specific promoters via interaction with other proteins such as Retinoblastoma. It will be important to isolate full length cDNA clones for protein expression in vitro and for use in the generation of antibodies and the biochemical binding of gene-specific probes for use in the characterization of gene expression by RNA blot analysis and transcript profiling. High-throughput methods for large scale RNA profiling can be used to detect changes in transcription during the disease response, and detection of HDs, MSIs, and the genes they may regulate will be included in these studies.

B. Functional characterization of HD/MSI function by mutational analysis.

The function of the HD and MSI genes in planta will be elucidated by the characterization of mutant alleles isolated by TUSC screening. This method has already proven useful in the isolation of ZmMSI1 disrupted alleles. HD and MSI specific primers can be designed that will amplify a number of gene family members, thus greatly reducing the number of PCR reactions required and allowing for the quick isolation of multiple alleles that can be characterized easily by genomic DNA blot and sequence analysis. The exact site of Mu insertion will be determined by sequencing genomic DNA amplified from wildtype (wt) and Mu-disrupted alleles using PCR methods. The expression patterns of all Mu-disrupted alleles will be compared to the basic patterns of expression of these genes in the wt plant to determine if any stable transcripts are present, thereby characterizing the nature of the mutation. Lines carrying the Mu-disrupted ZmMSI1 alleles for RNA isolation from tissues normally expressing ZmMSI1 are being propagated to determine if they are nullizygous in nature.

To alleviate problems of expressivity, an introgression series will be initiated with the introduction of each Mu-disrupted allele into a number of well-characterized inbred lines (W23, B73 and Mol7). At each generation, heterozygous mutants will also be self-fertilized to generate homozygous mutants, which can be assayed in the following studies. All Mu-disrupted alleles isolated will be crossed to generate pertinent double mutants, which may be more affected in these assays. Mutant plants under analysis will always be compared to control siblings, segregating as a result of this cross, carrying wt HD and MSI loci in the same genetic background.

1. Sensitivity to *C. carbonum* strains incapable of producing HC-toxin (TOX2$^-$).

Initial RNA profiling experiments have identified 91 maize genes that exhibit altered mRNA accumulation six hours after infection of hm mutant plants by *C. carbonum* TOX2$^-$. Of the genes showing increased expression, 14 were unaffected by application of purified HC-toxin during the fungal infection. Thirty-four other induced genes, however, did not respond in the presence of HC-toxin and thus are candidates for components of the defense response pathway that are regulated directly or indirectly by histone deacetylase. Similar results were observed among genes repressed during *C. carbonum* TOX2$^-$ infection. This illustrates the consequences of inhibiting histone deacetylase on gene expression during a defense response and indicates HD regulation of that response may involve both transcription induction and suppression.

Wt plants, regardless of Hm genotype, are resistant to TOX2$^-$-strains. Upon infection, elicitation occurs, pathogen defense genes are induced and only non-expanding lesions are produced. Assuming the HD or p48/MSI co-regulators act upstream of defense gene activation, the loss of expression of an HD or p48/MSI or other co-regulator protein that is a part of a complex normally targeted by HC-toxin would result in a plant that is now incapable of defense gene activation and susceptible to *C. carbonum* even in the absence of HC-toxin. The presence of HC-toxin reductase encoded by the Hm locus, typically present in the genetic background of the various Mu lines in the collection, will be inconsequential as no HC-toxin is produced by the pathogen. Sensitivity to *C. carbonum can be easily assayed by measuring lesion expansion. This study will directly identify HD or p48/MSI or other co-regulator loci regulating defense gene activation.*

2. An increased sensitivity to *C. carbonum* TOX2$^+$ strains.

Similar to above, plants carrying Mu-disrupted alleles of HD and p48/MSI co-regulator proteins necessary for defense gene activation may show increased sensitivity to infectious (HC-toxin producing; TOX2$^+$) strains of *C. carbonum*. One TUSC line known to have a disruption at one of the maize MSI genes has exhibited such sensitivity; while plants with the parental genotypes can resist *C. carbonum* TOX2$^+$ some plants from this mutated line show delayed disease symptoms after four days of infection.

3. General phenotype.

Morphologies of the vegetative and floral structures will be assessed compared to non-mutant sibling plants. As the Mu-background is reduced by outcrossing into inbred lines, it may be possible to detect characteristic phenotypes, that segregate with the tagged allele under investigation, indicating a role for these genes in normal development.

A. Biochemical characterization of HD/MSI complexes in vivo.

With the HD family members in hand, the tools useful for biochemical dissection of the complexes within which they function can be generated. Differentially-tagged versions of full length HD and MSI proteins will be expressed in *E. coli,* the yeast Pichia or in insect cells using a baculovirus system. Methods are available in the art for these systems. These proteins will be used to test association in in vitro binding assays to generate polyclonal antibodies for future use in in vitro co-precipitation assays. An initial study has been performed using a maize MSI1 protein fused to the GST protein and expressed in *E. coli*. This construct was immobilized to chromatography resin, and in vitro transcribed and translated ZmHD proteins were radiolabeled and passed over the resin. Analysis of the protein fractions that were retained during chromatography shows that ZmHD1b and 1c, but not 1a, interact with ZmMSI1 in this system. Such immobilized protein chromatography assays (binding assays) will also be used in combination with alanine scan or domain targeted mutants to map sites of interaction between the MSI and HD proteins.

Example 2

Transformation and Regeneration of Transgenic Plants

An HD nucleotide sequence is cloned into a plant expression vector as shown in FIG. 1. The nucleotide sequence is under transcriptional control of the maize ubiquitin promoter.

Immature maize embryos from greenhouse donor plants are bombarded with the plasmid containing the HD sequence operably linked to the ubiquitin promoter plus a plasmid containing the selectable marker gene PAT (Wohlleben et al. (1988) *Gene* 70: 25–37) that confers resistance to the herbicide Bialaphos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the HD nucleotide sequence operably linked to the ubiquitin promoter is made. This plasmid DNA plus plasmid DNA containing a PAT selectable marker is precipitated onto 1.1 $\mu$m (average diameter) tungsten pellets using a CaCl$_2$ precipitation procedure as follows:

100 $\mu$l prepared tungsten particles in water

10 $\mu$l (1 $\mu$g) DNA in TrisEDTA buffer (1 $\mu$g total)

100 $\mu$l 2.5 M CaCl$_2$

10 $\mu$l 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for enhanced disease resistance.

| Ingredient | Amount | Unit |
|---|---|---|
| D-I H₂O | 950.000 | ml |
| MS Salts (GIBCO 11117-074) | 4.300 | g |
| Myo-Inositol | 0.100 | g |
| MS Vitamins Stock Solution ## | 5.000 | ml |
| Sucrose | 40.000 | g |
| Bacto-Agar @ | 6.000 | g |

Directions:
@ = Add after bringing up to volume
Dissolve ingredients in polished D-I H₂O in sequence
Adjust to pH 5.6
Bring up to volume with polished D-I H₂O after adjusting pH
Sterilize and cool to 60° C.
## = Dissolve 0.100 g of Nicotinic Acid; 0.020 g of Thiamine.HCL; 0.100 g of Pyridoxine.HCL; and 0.400 g of Glycine in 875.00 ml of polished D-I H₂O in sequence. Bring up to volume with polished D-I H₂O. Make in 400 ml portions. Thiamine.HCL & Pyridoxine.HCL are in Dark Desiccator. Store for one month, unless contamination or precipitation occurs, then make fresh stock.
Total Volume (L) = 1.00

| Ingredient | Amount | Unit |
|---|---|---|
| D-I H₂O | 950.000 | ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| .1 mM Abscisic Acid | 1.000 | ml |
| Bialaphos 1 mg/ml # | 3.000 | ml |

Directions:
@ = Add after bringing up to volume
Dissolve ingredients in polished D-I H₂O in sequence
Adjust to pH 5.6
Bring up to volume with polished D-I H₂O after adjusting pH
Sterilize and cool to 60° C.
Add 3.5 g/L of Gelrite for cell biology.
## = Dissolve 0.100 g of Nicotinic Acid; 0.020 g of Thiamine.HCL; 0.100 g of Pyridoxine.HCL; and 0.400 g of Glycine in 875.00 ml of polished D-I H₂O in sequence. Bring up to volume with polished D-I H₂O. Make in 400 ml portions. Thiamine.HCL & Pyridoxine.HCL are in Dark Desiccator. Store for one month, unless contamination or precipitation occurs, then make fresh stock.
Total Volume (L) = 1.00

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:
@ = Add after bringing up to volume
# = Add after sterilizing and cooling to temp.
Dissolve ingredients in D-I H₂O in sequence
Adjust to pH 5.8 with KOH
Bring up to volume with D-I H₂O
Sterilize and cool to room temp.
Total Volume (L) = 1.00

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 120.000 | g |
| 2,4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:
@ = Add after bringing up to volume
# = Add after sterilizing and cooling to temp.
Dissolve ingredients in D-I H₂O in sequence
Adjust to pH 5.8 with KOH
Bring up to volume with D-I H₂O
Sterilize and cool to room temp.
 Autoclave less time because of increased sucrose
Total Volume (L) = 1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appeded claims.

That which is claimed:

1. An isolated polypeptide comprising an amino acid sequence selected from the group consisting of:
   (a) an amino acid sequence set forth in SEQ ID NO: 2, 4, 6, 8, 10, 12, 14, 16, or 18; and
   (b) an amino acid sequence selected from the group consisting of the amino acid sequences encoded by the cDNA inserts of the plasmids deposited as ATCC Accession Nos. 98720, 98719, 98717, 98718, 207183, 98716, 98723, 98722, and 98721.

2. An enzyme preparation comprising one of the amino acid sequences of claim 1, wherein said enzyme preparation enhances disease resistance in a plant.

3. An antibody that selectively binds to an isolated polypeptide comprising an amino acid selected from the group consisting of:
   (a) an amino acid sequence set forth in SEQ ID NO: 2, 4, 6, 8, 10, 12, 14, 16, or 18; and
   (b) an amino acid sequence selected from the group consisting of the amino acid sequences encoded by the cDNA inserts of the plasmids deposited as ATCC Accession Nos. 98720, 98719, 98717, 98718, 207183, 98716, 98723, 98722, and 98721.

4. An isolated polypeptide comprising at least 15 contiguous amino acids of the amino acid sequence selected from the group consisting of the amino acid sequence set forth in SEQ ID NO: 2, 4, 6, 8, 10, 12, 14, 16, and 18.

5. An isolated polypeptide comprising an amino acid sequence having at least 80% sequence identity to an amino acid sequence selected from the group consisting of the amino acid sequence set forth in SEQ ID NO: 2, 4, 6, 8, 10, 12, 14, 16, or 18.

6. The isolated polypeptide of claim 5, wherein said polypeptide has at least 85% sequence identity to an amino acid sequence selected from the group consisting of the amino acid sequence set forth in SEQ ID NO: 2, 4, 6, 8, 10, 12, 14, 16, or 18.

7. The isolated polypeptide of claim 6, wherein said polypeptide has at least 90% sequence identity to an amino acid sequence selected from the group consisting of the amino acid sequence set forth in SEQ ID NO: 2, 4, 6, 8, 10, 12, 14, 16, or 18.

8. The isolated polypeptide of claim 7, wherein said polypeptide has at least 95% sequence identity to an amino acid sequence selected from the group consisting of the amino acid sequence set forth in SEQ ID NO: 2, 4, 6, 8, 10, 12, 14, 16, or 18.

9. An antibody that selectively binds to an isolated polypeptide comprising at least 15 contiguous amino acids of the amino acid sequence set forth in SEQ ID NO: 2, 4, 6, 8, 10, 12, 14, 16, or 18.

* * * * *

UNITED STATES PATENT AND TRADEMARK OFFICE
CERTIFICATE OF CORRECTION

PATENT NO. : 6,479,629 B2
DATED : November 12, 2002
INVENTOR(S) : Baldwin et al.

It is certified that error appears in the above-identified patent and that said Letters Patent is hereby corrected as shown below:

Title page,
Item [75], Inventors, in the third inventor's address, "Des Moines, CA" should read -- Des Moines, IA --.

Column 23,
Insert -- Appendix -- before line 1 in Column 23;
Before the first chart, insert sub-heading -- 272V --;
Before the second chart, insert sub-heading -- 288J --;
Before the third chart, insert sub-heading -- 560R --.

Column 24,
Before the fourth chart, insert sub-heading -- 560Y --.

Column 71,
Line 17, "and" should read -- or --.

Signed and Sealed this

Twenty-seventh Day of May, 2003

JAMES E. ROGAN
*Director of the United States Patent and Trademark Office*